(12) United States Patent
Nunoshige et al.

(10) Patent No.: US 10,024,828 B2
(45) Date of Patent: Jul. 17, 2018

(54) ADSORBENT AND ANALYSIS METHOD USING SAME

(71) Applicant: Hitachi High-Technologies Corporation, Minato-ku, Tokyo (JP)

(72) Inventors: Jun Nunoshige, Tokyo (JP); Shinya Ito, Tokyo (JP); Hiroshi Nakano, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 224 days.

(21) Appl. No.: 14/894,633

(22) PCT Filed: May 7, 2014

(86) PCT No.: PCT/JP2014/062237
§ 371 (c)(1),
(2) Date: Nov. 30, 2015

(87) PCT Pub. No.: WO2014/199746
PCT Pub. Date: Dec. 18, 2014

(65) Prior Publication Data
US 2016/0109417 A1      Apr. 21, 2016

(30) Foreign Application Priority Data

Jun. 14, 2013   (JP) ................... 2013-125505

(51) Int. Cl.
*B01J 20/281*   (2006.01)
*B01J 20/28*    (2006.01)
(Continued)

(52) U.S. Cl.
CPC ........... *G01N 30/482* (2013.01); *B01D 15/08* (2013.01); *B01J 20/288* (2013.01);
(Continued)

(58) Field of Classification Search
CPC .............. B01D 15/08; B01J 20/28019; B01J 20/28042; B01J 20/288; B01J 20/321;
(Continued)

(56) References Cited

U.S. PATENT DOCUMENTS

| 5,618,438 A | 4/1997 | Fritz et al. |
| 2005/0093189 A1 * | 5/2005 | Vo .......................... B01D 53/64 264/29.1 |

(Continued)

FOREIGN PATENT DOCUMENTS

| JP | 53-23891 | 3/1978 |
| JP | S 5323891 | * 3/1978 ............ Y02P 10/234 |

(Continued)

OTHER PUBLICATIONS

International Search Report (PCT/ISA/210) issued in PCT Application No. PCT/JP2014/062237 dated Aug. 12, 2014, with English translation (two (2) pages).

(Continued)

*Primary Examiner* — Jennifer Wecker
(74) *Attorney, Agent, or Firm* — Crowell & Moring LLP

(57) ABSTRACT

An adsorbent which enables solid phase extraction of water-soluble molecules with high efficiency and excellent selectivity and an analysis system using the adsorbent, the adsorbent containing a structure represented by the formula I (I)

(Continued)

wherein R is a carrier component, the moiety other than R is a side-chain functional group, R and the benzene ring in the side-chain functional group are bonded directly or bonded through one or more atoms, R' is selected from the group consisting of hydroxy group, alkoxy group, amino group, alkylamino group, thiol group and alkyl sulfide group, R" is independently selected from the group consisting of hydroxy group, alkoxy group, alkyl group, amino group, alkylamino group, dialkylamino group, trialkylamino group, thiol group, alkyl sulfide group and hydrogen atom, x is an integer of zero or more and three or less, and n is the number of the side-chain functional groups contained in the carrier component.

13 Claims, 4 Drawing Sheets

(51) Int. Cl.
  $B01D\ 15/08$ (2006.01)
  $G01N\ 30/52$ (2006.01)
  $B01J\ 20/288$ (2006.01)
  $B01J\ 20/32$ (2006.01)
  $G01N\ 30/72$ (2006.01)
  $G01N\ 30/00$ (2006.01)
  $G01N\ 30/02$ (2006.01)

(52) U.S. Cl.
  CPC ...  *B01J 20/28019* (2013.01); *B01J 20/28042* (2013.01); *B01J 20/321* (2013.01); *B01J 20/3212* (2013.01); *B01J 20/3248* (2013.01); *B01J 20/3253* (2013.01); *G01N 30/52* (2013.01); *B01J 2220/54* (2013.01); *B01J 2220/82* (2013.01); *G01N 30/72* (2013.01); *G01N 2030/009* (2013.01); *G01N 2030/027* (2013.01); *G01N 2030/484* (2013.01)

(58) Field of Classification Search
  CPC ............ B01J 20/3212; B01J 20/3248; B01J 20/3253; B01J 2220/54; B01J 2220/82; G01N 2030/009; G01N 2030/027; G01N 2030/484; G01N 30/482; G01N 30/52; G01N 30/72
  See application file for complete search history.

(56) References Cited

U.S. PATENT DOCUMENTS

| | | | | |
|---|---|---|---|---|
| 2011/0247981 | A1* | 10/2011 | Ono | B01D 15/327 210/662 |
| 2013/0048853 | A1* | 2/2013 | Nunoshige | B01J 20/285 250/288 |
| 2014/0378705 | A1 | 12/2014 | Hamase et al. | |

FOREIGN PATENT DOCUMENTS

| | | |
|---|---|---|
| JP | 2000-55897 A | 2/2000 |
| WO | WO 97/38774 A2 | 10/1997 |
| WO | WO 2013/115334 A1 | 8/2013 |

OTHER PUBLICATIONS

Japanese-language Written Opinion (PCT/ISA/237) dated Aug. 12, 2014, (three (3) pages).
Patrick D. McDonald, Solid Phase Extraction Applications Guide and Bibliography, sixth edition, 1995 (83 pages).

* cited by examiner

ADSORBENT AND ANALYSIS METHOD USING SAME

TECHNICAL FIELD

The present invention relates to an adsorbent and an analysis system using the adsorbent.

BACKGROUND ART

A drug administration method referred to as therapeutic drug monitoring (TDM) which is used for medicines with strong side effects draws attention. TDM is medical technology for measuring the blood concentration of a drug in each individual patient and thus determining the dosage and direction to satisfy the desirable effective therapeutic concentration for the patient.

Immunoassay using an antibody against the medicine to be measured and separation and analysis methods using mass spectrometry (MS), high performance liquid chromatography (HPLC) and the like are mainly used for measuring the blood concentration of a drug in TDM. As a technique to compensate the decrease in the sensitivity of MS analysis and the like, a method of pretreating a sample through solid phase extraction (SPE) has been proposed in (NPL 1). Solid phase extraction can reduce the influence of impurities on a quantitative analysis. Accordingly, solid phase extraction, as a useful separation technique, is a useful method for analysis of trace amounts of organic compounds, for example microanalysis of water quality, soil or the like, for quantitative analysis of trace amounts of additives, poisonous substances, agricultural chemicals or the like and the like, as well as for the pretreatment in TDM, and solid phase extraction is used in a wide range of fields including environmental pollution, drug development, evaluation of food nutrition, evaluation of nutrition of functional foods, evaluation of purity of drinking water and biotechnology.

As examples of adsorbents that are widely used for solid phase extraction, silica particles and porous silica particles with surface modified with hydrophobic octyl (C8) functional group, octadecyl (C18) functional group or the like are known. However, when the solvation of the adsorbent with a polar organic solvent is insufficient or when the adsorbent is dry, aggregation of hydrophobic functional groups deteriorates the ability to hold the solute, and the separation through solid phase extraction is difficult. Accordingly, it is necessary to keep the adsorbent surface always in the state of being sufficiently solvated with the polar organic solvent (conditioning) when solid phase extraction is performed.

As an example of an adsorbent which replaces silica, resin particles having styrene-divinylbenzene or methacrylic acid ester as the main chain are known (PTL 1). Because the resin particles are more stable against the influence of pH and ionic strength than silica particles and have a broader surface area, the level of ability to hold the solute is higher than that of silica particles. On the other hand, because the surface is a hydrophobic surface, a complicated operation such as conditioning with a polar organic solvent is necessary as the silica particles with modified surface. Moreover, all of the types of particle have their drawbacks because the ability to hold the solute changes with the polarity of the solute and the conditions of solid phase extraction and the reliability of the measurement varies with the conditions of solid phase extraction.

As a method for decreasing the hydrophobicity of the resin particles, (PTL 2) discloses a method using an adsorbent of a hydrophobic-hydrophilic monomer copolymer obtained by introducing a hydrophilic monomer such as N-vinylpyrrolidone or vinylpyridine to a hydrophobic monomer such as divinylbenzene. Examples of a copolymer of divinylbenzene and N-vinylpyrrolidone include OASIS (registered trademark) HLB manufactured by Waters Corporation and the like. Because the adsorbent contains a hydrophilic molecular structure, the wettability between a polar solvent such as water and the adsorbent improves, and the level of ability of the hydrophilic group to hold the solvent is high. Therefore, the excessive conditioning is not necessary. However, the adsorbent surface cannot sufficiently hold a compound with a highly polar structure, such as some medicines (for example, medicines with a cyclic structure and a large molecular weight and the like) and metabolites of medicines, and thus polar solute molecules are desorbed and eluted, which is not intended, during the step of introducing the medicine solution to the adsorbent and/or the washing step. This results in the decrease in the recovery rate of the solute. In particular, the recovery rate decreases in solid phase extraction of moderately or highly polar solute molecules, and the loss of the sample during the solid phase extraction is great. As a result, the reliability of the analysis is deteriorated. It is presumed that this is because the hydrophilic adsorption sites of the copolymer are small and isolated, and strong adsorption of molecules through hydrophilic interaction cannot be caused, resulting in weak adsorption of highly polar molecules. In addition, it is considered that the hydrophilic side-chain functional group contained in the adsorbent, which has a bulky structure, causes steric hindrance when the medicine is adsorbed and thus decreases the recovery rate of the solute.

CITATION LIST

Non Patent Literature

NPL 1: P. McDonald, Solid Phase Extraction Applications Guide and Bibliography, sixth edition, Waters, Milford, Mass. (1995)

Patent Literature

PTL 1: U.S. Pat. No. 5,618,438
PTL 2: WO97/38774

SUMMARY OF INVENTION

Technical Problem

When the adsorbent described in (PTL 2) is used, conditioning can be simplified due to the improved wettability on the adsorbent surface, and solid phase extraction with excellent process property is possible. However, adsorption through sufficient hydrophilic interaction between the solute such as a medicine and the hydrophilic structure cannot be caused, and the sample recovery amount of solid phase extraction tends to decrease as the polarity of molecules becomes higher. Moreover, the adsorbent hardly adsorbs molecules which dissolve in water (water-soluble molecules) for example, and solid phase extraction of these molecules is not possible. Medicines which are analyzed by TDM include substances that correspond to water-soluble molecules. Thus, to monitor a wider range of medicines, development of an adsorbent that enables highly efficient solid phase extraction of these medicines is strongly required.

Thus, the invention aims to provide an adsorbent which enables solid phase extraction of water-soluble molecules with high efficiency and excellent selectivity and an analysis system using the adsorbent.

Solution to Problem

The present inventors have conducted intensive studies on adsorbents which would allow solid phase extraction of water-soluble molecules and found that solid phase extraction of water-soluble molecules is possible by using an adsorbent containing an aromatic side-chain functional group in which an electron donating functional group such as hydroxy group and nitro group are directly bonded to one aromatic ring. The invention has been thus completed. That is, the adsorbent of the invention is characterized by containing a structure represented by the formula I

[Chem. 1]

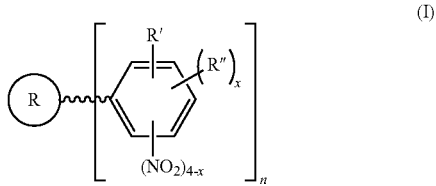

(in the formula I, R is a carrier component, the moiety other than R is a side-chain functional group, R and the benzene ring in the side-chain functional group are bonded directly or bonded through one or more atoms, R' is selected from the group consisting of hydroxy group, alkoxy group, amino group, alkylamino group, thiol group and alkyl sulfide group, R'' is independently selected from the group consisting of hydroxy group, alkoxy group, alkyl group, amino group, alkylamino group, dialkylamino group, trialkylamino group, thiol group, alkyl sulfide group and hydrogen atom, x is an integer of zero or more and three or less, and n is the number of the side-chain functional groups contained in the carrier component.)

The present description includes the contents described in the description and/or the drawings of Japanese Patent Application No. 2013-125505, which is the priority application of the present application.

Advantageous Effects of Invention

The adsorbent of the invention has an aromatic side-chain functional group with a special structure, and it is thus possible to highly efficiently and selectively separate and recover solutes with a wide range of chromatographic polarity including water-soluble solute molecules, which cannot be recovered with the conventional adsorbents. Moreover, when solid phase extraction using the adsorbent is performed as pretreatment in an analysis system, a solute such as water-soluble molecules in a sample can be analyzed efficiently. Aims, constitutions and effects other than those described above are disclosed in the following explanations of embodiments.

DESCRIPTION OF EMBODIMENTS

Figure 1:
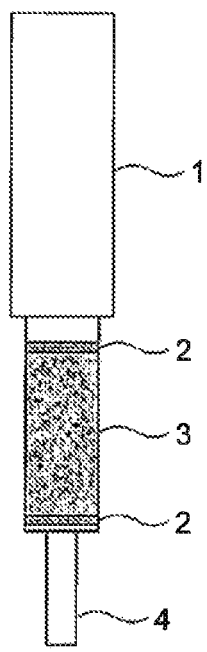
FIG. 1 A figure showing an embodiment of the solid phase extraction cartridge of the invention.

The invention is explained in detail below.

The adsorbent of the invention contains a structure having an aromatic side-chain functional group. When the structure is brought into contact with a sample containing organic molecules as the solutes, one or more kinds of solute in the sample can be adsorbed and held. The invention is characterized in that the aromatic side-chain functional group has an electron donating group such as hydroxy group and nitro group, which is an electron withdrawing group.

The electron donating group generally has an effect of increasing the electron density of the benzene ring contained in the side-chain functional group. Moreover, possible electron withdrawing groups also include sulfo group, cyano group and the like, in addition to nitro group, but the functional group which achieved the effects of the invention was nitro group. When nitro group is bonded to a benzene ring, the nitro group forms various resonance structures, and electrons are likely to gather around the nitro group. The combination of nitro group and an electron donating group further facilitates the polarization in the molecule, and this leads to an adsorbent which is suitable for the adsorption of a solute which easily dissolves in water, namely a solute with a low log P value explained below.

Specifically, the adsorbent of the invention contains a structure represented by the formula I.

[Chem. 2]

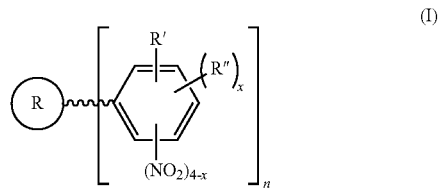

In the formula I, R is a carrier component. The moiety other than R is a side-chain functional group, and R and the benzene ring in the side-chain functional group are bonded directly or bonded through one or more atoms. R' is selected from the group consisting of hydroxy group, alkoxy group, amino group, alkylamino group, thiol group and alkyl sulfide group, and R'' is independently selected from the group consisting of hydroxy group, alkoxy group, alkyl group, amino group, alkylamino group, dialkylamino group, trialkylamino group, thiol group, alkyl sulfide group and hydrogen atom. x is an integer of zero or more and three or less, and n is the number of the side-chain functional groups contained in the carrier component. Moreover, among the substituents of R' and R'', when the functional groups contain alkyl group or alkyl group structure, the alkyl group is preferably a linear or branched group having one to six carbon atoms.

The side-chain functional groups may be on the surface of the structure, inside thereof or both on the surface and inside thereof, and the molecular structures of the side-chain functional groups may be the same or different from each other. In case of a porous structure, the properties of the side-chain functional groups can be used efficiently when the side-chain functional groups are also inside the structure. Moreover, the molecular structures of the respective structures may be the same or different from each other. Furthermore, the side-chain functional groups and the structures may have a distribution of molecular weights.

The carrier component R in the structure is not particularly limited as long as it is a carrier capable of holding the side-chain functional groups in the formula I, such as inorganic compounds including silicon oxide, aluminum oxide and the like and polymers (resins) of organic compounds. For example, the structure of the formula I can be formed by modifying a cross-linked polystyrene resin or the like with a functional group. The carrier component and the side-chain functional group may be bonded directly or bonded through one or more atoms. For example, the carrier component and the side-chain functional group may be bonded through a reactive molecule by silane coupling, an addition reaction or the like. In order to increase the frequency of contact between the carrier and the solute, the carrier desirably has a porous structure with a large surface area.

More preferably, the adsorbent of the invention contains a resin structure prepared by copolymerization of a monomer component which constitutes a carrier capable of holding or forming a side-chain functional group and another monomer component.

As the other monomer, a monomer having one or more functional groups which can be copolymerized with the monomer having a side-chain functional group is preferably used. Specific examples of the monomer include aromatic vinyl compounds such as styrene, vinyltoluene, α-methylstyrene, m-divinylbenzene, p-divinylbenzene, 1,2-diisopropenylbenzene, 1,3-diisopropenylbenzene, 1,4-diisopropenylbenzene, 1,3-divinylnaphthalene, 1,8-divinylnaphthalene, 1,4-divinylnaphthalene, 1,5-divinylnaphthalene, 2,3-divinylnaphthalene, 2,7-divinylnaphthalene, 2,6-divinylnaphthalene, 4,4'-divinylbiphenyl, 4,3'-divinylbiphenyl, 4,2'-divinylbiphenyl, 3,2'-divinylbiphenyl, 3,3'-divinylbiphenyl, 2,2'-divinylbiphenyl, 2,4-divinylbiphenyl, 1,2-divinyl-3,4-dimethylbenzene, 1,3-divinyl-4,5,8-tributylnaphthalene, 2,2'-divinyl-4-ethyl-4'-propylbiphenyl, bisvinylphenyl ethane, 1,2,4-trivinylbenzene, 1,3,5-trivinylbenzene, 1,2,4-triisopropenylbenzene, 1,3,5-triisopropenylbenzene, 1,3,5-trivinylnaphthalene and 3,5,4'-trivinylbiphenyl, unsaturated carboxylic acid esters such as methyl (meth)acrylate, 2-hydroxyethyl (meth)acrylate, t-butyl (meth)acrylate, n-hexyl (meth)acrylate, cyclohexyl (meth)acrylate, 2-ethylhexyl (meth)acrylate, lauryl (meth)acrylate, stearyl (meth)acrylate, benzyl (meth)acrylate, (poly)ethylene glycol mono- or di(meth)acrylate, (poly)propylene glycol mono- or di(meth)acrylate, 1,4-butanediol mono- or di-(meth)acrylate and trimethylolpropane mono-, di- or tri-(meth)acrylate, allyl compounds such as allyl glycidyl ether, vinyl acetate, bisvinylphenyl ethane, diallyl phthalate, diallyl acrylamide, triallyl(iso)cyanurate and triallyl trimellitate, (poly)oxyalkylene glycol di(meth)acrylates such as (poly)ethylene glycol di(meth)acrylate and (poly)propylene glycol di(meth)acrylate and the like. Moreover, monomers such as acrylic acid, methacrylic acid, itaconic acid, fumaric acid, glycidyl methacrylate, vinylpyridine, diethylaminoethyl acrylate, N-methylmethacrylamide and acrylonitrile are mentioned, but the monomer is not limited to the examples. Any one kind or a combination of two or more kinds of the monomers can be appropriately selected depending on the structure of the adsorbent and desired physical properties, and as a result an adsorbent more suitable for solid phase extraction can be provided. Moreover, a stronger cross-linked network structure is formed in the resin, and an adsorbent with excellent mechanical strength and thermal stability can be obtained. In addition, swelling due to a solvent or the like can be prevented, and the deformation, denaturation, softening, dissolution and the like of the adsorbent can be prevented.

The resin structure can be formed by known copolymerization. Examples thereof include random polymerization, alternating copolymerization, block copolymerization and graft polymerization. Among the polymerization methods, random polymerization and alternating copolymerization, in which the control over the polymerization is easy, are particularly preferably used. The side-chain functional group can be formed by known methods. In an example method, according to the method described in K. Lewandowski, F. Svec and M. J. Frechet, A Novel Polar Separation Medium for the Size Exclusion Chromatography of Small Molecules: Uniformly Sized, Porous Poly(vinylphenol-co-divinylbenzene) Beads, J. Liq. Chrom. & Rel. Technol., 20(2), 227-243 (1997), a copolymer having a phenol side chain is prepared, and then nitration with nitric acid or a mixed acid of sulfuric acid and nitric acid is performed. By this method, a side-chain functional group having a nitrophenol structure, which is a constituent structure of the invention, can be formed. In another example, a part of cross-linked polystyrene is nitrated with a mixed acid of sulfuric acid and nitric acid and then reduced in hydrochloric acid-iron catalyst to introduce an aniline structure to the side chain, the aniline is acetylated in the presence of acetic anhydride and then nitrated with nitric acid or a mixed acid of sulfuric acid and nitric acid, and the acetyl protecting group is removed through hydrolysis. By this method, a side-chain functional group having a nitroaniline structure, which is a constituent structure of the invention, can be formed. In both cases, structural isomers and structures with different numbers of substituents may be contained, and the structure can be controlled by the treatment method or the conditions. The number of the nitro groups contained in the side-chain functional group of the formula I and the method for introducing the nitro groups are not particularly limited, and the number and the method can be appropriately adjusted depending on the kind of solute. The number of the nitro groups contained in the formula I, (4-x), is desirably in the range of one to four (x=0 to 3), more desirably one or two (x=2 or 3).

The resin structure can be prepared by known polymerization methods. Examples thereof are suspension polymerization, emulsification polymerization, emulsion polymerization, spray drying method, pulverization, crushing, bulk polymerization, solution polymerization and the like. Among the polymerization methods, in order to improve the reproducibility of the adsorption performance, a method by which uniform spherical particles can be obtained is more preferable, and suspension polymerization and emulsification polymerization are more preferably used. In addition, steps involving ring-opening reaction, dehydration condensation, intermolecular binding and other changes of the intramolecular structure may be included in the polymerization and other treatment processes, and the invention is not particularly limited in this regard.

The copolymerization ratio of the monomer having the side-chain functional group of the invention and the other monomer varies with the kinds of the monomers and is not particularly limited. However, when the ratio of the monomer having the side-chain functional group is too low, the effects of the invention are not obtained. Thus, the ratio is appropriately determined taking these points into consideration. For example, it is preferable that the repeating unit derived from the monomer component having the side-chain functional group accounts for 5 mol % or more of the copolymer, particularly 10 mol % or more.

The adsorption in the invention means the state in which the solute and the adsorbent are bonded to each other reversibly through the interaction between the molecules. The intermolecular interaction mainly refers to all the intermolecular forces in which a polar structure is involved, such as hydrogen bond, dipole-dipole interaction, ion-dipole interaction, dipole-induced dipole interaction and London dispersion force.

The solute containing water-soluble molecules contain many atoms with a high electronegativity, and the degree of intramolecular polarization is higher as the degree of solubility of the molecules in water is higher. In the invention, the property of adsorbing water-soluble molecules is acquired by introducing a molecular structure which has a high electronegativity like the water-soluble molecules and which matches the polarized structure of the water-soluble molecules. That is, by introducing an aromatic side-chain functional group to which an electron donating functional group and nitro group are directly bonded into the molecular structure of the adsorbent, it has been achieved to form a side-chain molecular structure which is suitable for the adsorption.

In the invention, the polarity of the solute is defined as follows based on the octanol-water partition coefficient (log P). The water-soluble solute molecule means a molecule having a log P value around 0 or a negative log P value. The log P value numerically expresses the polarity of the solute, and a value calculated from the molecular structure and a measured value can be both used. In this regard, even when the log P value is 0 or larger, a molecule which is locally polarized to a great degree sometimes shows behavior similar to those of water-soluble molecules. Examples of the water-soluble solute molecules which can be adsorbed to the adsorbent of the invention include gemcitabine (log P=0.14), theophylline (log P=−0.25), 5-fluorouracil (log P=−0.57), methotrexate (MTX) (log P=−0.91), tenofovir (log P=−1.5), cytarabine (log P=−2.7) and the like. Moreover, the adsorbent similarly has solid phase extraction performance also with respect to solute molecules which are not within the scope of the water-soluble molecules but which have high polarity, such as phenobarbital (log P=1.7), phenytoin (log P=2.5), carbamazepine (log P=2.5) and diazepam (log P=2.9). The subjects to which the adsorbent of the invention is applied are not limited by the range of the log P values of the solute molecules, but the adsorbent has solid phase extraction performance with respect to solute molecules having a log P value in the range of around −3.0 to 3.0.

The solute to which the adsorbent of the invention is applied is a substance which should be recovered by solid phase extraction and is not particularly limited. Preferable subject solutes are the water-soluble organic molecules and specifically include a wide range of substances including substances with pharmacological effects such as medicaments, medicines, antibacterial agents, antiviral agents, anticancer agents, drugs, insecticides, herbicides, poisonous substances, biomolecules, proteins, vitamins, hormones, polypeptides, polynucleotides, lipids, carbohydrates, contaminated substances, metabolic agents, degraded metabolites, antiepileptic agents, immunosuppressive agents, antioxidants, anti-inflammatory agents, agents for improving blood circulation, skin lightening agents, agents for preventing rough skin, antiaging agents, trichogenous agents, moisturizing agents and vaccine preparations, substances without pharmacological effects such as dyes/fluorescent dyes, chelating agents, stabilizers and preservatives and the like.

The adsorbent of the invention preferably has spherical or aggregated particulate size and shape. In order to secure the specific surface area and to secure a moderate packing density of the adsorbent, the 50% mean particle size of the adsorbent particles is preferably in the range of 0.5 μm to 100 μm. When the particle size is too large, the solution flows out before the solute is adsorbed in the process of introducing the solution. Moreover, the effective surface area of the adsorbent is small, and satisfactory solid phase extraction performance cannot be exhibited. On the other hand, when the particle size is too small, the pressure drop in the flow path increases considerably, and the efficiency of solid phase extraction decreases. The 50% mean particle size of the particles is more preferably in the range of 1 μm to 90 μm, further preferably in the range of 10 μm to 80 μm.

In addition, with respect to the conditions of the solid phase extraction in the invention, the adsorbent has a tendency not to have satisfactory solid phase extraction performance also when the proportion of particles with a size of 100 μm or more in the adsorbent particles is high. As a result of intensive studies on the conditions of the solid phase extraction, it has been found that the extraction efficiency increases further when the particle size distribution of the adsorbent particles is controlled and the content of particles with a size of 100 μm or more is decreased. Specifically, a more desirable particle distribution condition is a 50% mean particle size of the particles of 0.5 μm to 80 μm and an 80% mean particle size of 0.5 pin to 100 μm. When the particles satisfy the condition, the solution penetrates into the particles, and the effective surface area of the adsorbent involving the adsorption becomes larger. As a result, adsorption of the solute with higher efficiency is possible. The particle distribution condition can be optimized for example by adjusting the polymerization condition in such a manner that the particle sizes fall within the set ranges or by applying known classification techniques (for example, classification sieving, wet classification, dry classification and the like), although the method is not limited to the examples.

The adsorbent of the invention should have the specific side-chain functional group, and it is needless to mention that the adsorbent has solid phase extraction performance even when the adsorbent has a shape other than a particle shape. For example, when a porous bulky polymer prepared by bulk polymerization or solution polymerization is used, excellent solid phase extraction performance is exhibited. An example of such a porous bulky polymer is a monolithic polymeric porous structure which is integrated into the column and which reduces the pressure drop when a fluid passes through. Although it is necessary to adjust the size of the structure to the shape of the column, the connectivity of pores is high, and their sizes are uniform. Also, it is not necessary to consider the spaces and the like when the particles are packed. Accordingly, the adsorbent is manageable as compared to a particulate adsorbent. When the adsorbent is a polymeric porous film structure in a film shape prepared by bulk polymerization, solution polymerization or solid phase polymerization, the adsorbent can be applied for example to a carrier used in thin-layer chromatography or the like, a solid phase adsorption film for a simple test and the like. The adsorbent of the invention can exhibit adsorption performance due to the various shapes and forms above.

When the adsorbent of the invention is prepared, it is preferable not only to confirm that a side-chain functional group has been incorporated into the adsorbent but also to control the copolymerization ratio of the adsorbent and the whole structure thereof. In this regard, various measurement techniques, which are not limited, can be used. For example, to evaluate the adsorbent of the invention, Fourier transform infrared spectroscopy (FTIR), solid phase $^{13}C$ nuclear magnetic resonance, elementary analysis (by a combustion method) and the like can be used. These techniques are known and can be used to identify and analyze a structure.

Next, the method for isolating a solute from a sample using the adsorbent of the invention is explained. The sample to be measured is not particularly limited, but in general, the sample is a solution. The adsorbent of the invention is particularly suitable for isolating a solute to be measured from a sample for component analysis of a complex composition (microanalysis of water quality, soil or the like, quantitative analysis of trace amounts of additives, poisonous substances, agricultural chemicals or the like, evaluation of environmental pollution, drug development, evaluation of food nutrition, evaluation of nutrition of functional foods, evaluation of purity of drinking water, TDM analysis and the like). Examples of the sample include biogenic substrates containing a target solute such as medicines. Moreover, the sample includes an environmental sample such as drinking water or contaminated water. Specific examples of the sample include plasma, serum, blood, urine, spinal fluids, synovial fluids, tissue extracts, aqueous solutions, groundwater, surface water, soil extracts, cosmetics, food materials, extracts of food materials and the like.

The solid phase extraction for isolating a solute to be measured from a sample includes steps of bringing a solution containing the solute molecules into contact with the adsorbent and selectively adsorbing and holding the solute. More specifically, the solid phase extraction includes four general steps: a step of conditioning the adsorbent using a solvent which enhances the surface properties; a step of introducing the sample; a step of washing the adsorbent with a washing solvent (water or an organic solvent); and a step of desorbing the solute with an elution solvent (water or an organic solvent). The kinds of the solvent used for the conditioning, the washing solvent and the elution solvent are not particularly limited but are more preferably polar solvents from the viewpoint of maintenance of the hydrophilicity of the surface. Specifically, the solvents are water, polar organic solvents such as methanol, ethanol, propanol, 2-propanol, acetone, methyl ethyl ketone, methyl isobutyl ketone, methyl acetate, ethyl acetate, acetonitrile, tetrahydrofuran, 1,4-dioxane, N,N-dimethylformamide and dimethyl sulfoxide or hydrous solvents such as mixed solvents of the polar organic solvents and water.

In the conditioning process, the adsorbent surface can be conditioned by washing the adsorbent with a polar organic solvent and then washing the adsorbent with water. In a preferable example, the conditioning is performed by, after filling a support like a column with the adsorbent, first treating with methanol and then treating with water (for example, each in an amount of 1 ml). Methanol swells the adsorbent moderately and increases the effective surface area. Through the water treatment, excess methanol is removed and the surface is hydrated at the same time. As a result, the excess solvent is removed, and the adsorbent can keep the state of being completely hydrated.

When the sample to be analyzed by the solid phase extraction is a solution with a low viscosity, such as a medicine solution or whole blood components from which serum, protein components and the like have been removed, the sample can be introduced to the adsorbent without any particular treatment, while it is desirable to introduce an aqueous dilute solution of the sample (at least 1:1 dilution) when the sample contains a solution with a high viscosity such as plasma. In particular, because the viscosity of plasma is high, plasma may prevent the adsorption of the solute to the adsorbent. Moreover, proteins in the plasma components are sometimes denatured by an organic solvent and precipitate, and the adsorbent surface may be contaminated. Thus, dilution with an organic solvent is desirably avoided. Furthermore, it is desirable to adjust the flow rate of the sample solution so that the period suitable for adsorbing and holding the solute can be secured.

In an embodiment, the solute (for example, a medicine) can exist at a level of 1 ng to 10 µg per 1 mL of the sample. Moreover, the amount introduced to the solid phase extraction unit including the adsorbent depends on the volume of the adsorbent, but a sample in an amount of about 1 µL to 100 µL can be introduced in case of a solid phase extraction plate and a sample in an amount of about 100 µL to 1 mL can be introduced in case of a solid phase extraction column.

The adsorbent to which the solute is adsorbed can be then washed with water and an organic solvent. More preferably, the adsorbent is washed with water. Any amount of solvent can be used for washing, but a solvent in an amount of about 50 µL to 500 µL is preferably used. Through washing with water, a salt, any water-soluble substrate which may be contained in the sample and which is not to be measured and impurities such as a proteinous substance are removed. In addition, when the sample contains a substance constituting a substrate or organic impurities which are adhered to the adsorbent surface and which are insoluble in water, the substance and the organic impurities can be washed off and removed using an organic solvent. At this point, it is preferable to adjust the washing conditions so as not to disturb the adsorption of the solute to the adsorbent surface. When many conventional silica adsorbents and polymeric adsorbents are used for separation, a large amount of the solute to be measured may be removed from the adsorbent in the washing step.

Then, the solute is desorbed from the adsorbent surface using an elution solvent. The desorption is caused when the elution solvent reaches and touches the adsorption interface between the solute and the adsorbent and can be caused by applying a certain amount of elution solvent. Representative elution solvents are water, a polar organic solvent and an aqueous solution. The polar organic solvent desirably contains an organic component at least in an amount of about 80% by weight to 90% by weight. Representative polar organic solvents are alcohol solutions such as methanol, ethanol and 2-propanol, acetonitrile and the like, but the polar organic solvent is not limited to the solvents. It is known that trifluoroacetic acid and the like can also be used as the elution solvents and are useful for efficiently disturbing the polar interaction between the solute and the adsorbent. Any amount of solvent can be used for the elution, but for example a solvent in an amount of about 50 µL to 200 µL is preferably used in case of a solid phase extraction plate. Using the solvent, 90% to almost the total amount of the solute held by the adsorbent can be recovered.

With respect to the adsorbent of the invention, in some cases, the solute can be desorbed from the adsorbent surface without using a polar organic solvent. That is, it has been newly found that by applying an aqueous solution prepared by dissolving or dispersing a basic salt or compound as the elution solvent, the electron density of the aromatic side-chain functional group changes, and as a result, the color of the adsorbent and its molecular structure change. For example, it was confirmed that the colors of adsorbents having a nitrophenol structure as the side-chain functional group changed from yellow (yellowish brown) to red and that the specific surface areas and the pore sizes also changed significantly. Moreover, it was found that the adsorbents having a nitrophenol structure which turned into red through the treatment did not have a property of adsorbing water-soluble solutes, unlike the adsorbents before the treatment. It is presumed that this was because the adsorption performance of the adsorbents having a side-chain functional group changed by the influence of the basic elution solvent. In this regard, when an acidic solvent is applied, an adsorbent which has turned into red can be converted to a yellow (yellowish brown) adsorbent again, and adsorption performance comparable to that before applying a basic elution solvent can be regained. Using this property, by adjusting the acidity or basicity of the solvent, the adsorption-desorption of the solute to/from the adsorbent can be freely controlled, and the respective processes of adsorption, washing and desorption can be performed using water only as the solvent. The characteristics have not been observed with the conventional adsorbents, and this is a very useful technique as a solid phase extraction method without using an organic solvent, which has properties such as volatility and inflammability.

The degree of basicity of the elution solvent suitable for desorption varies with the kind of solute and the structure of the adsorbent, but it is desirable to use a basic elution solvent with a hydrogen ion exponent (pH) higher than 8.0, and the pH is further desirably 9.0 or higher. Because the solute and the adsorbent may be denatured when the pH of the basic elution solvent is too high, it is desirable to adjust the pH within a range which does not affect the solute and the adsorbent. Using the solvent, 90% to almost the total amount of the solute held by the adsorbent can be recovered.

Other examples of the method for desorbing the solute include methods using heat, vibrations, light irradiation and the like for example, and the methods can be appropriately used according to the structure of the side-chain functional group and its physical properties. Taking the versatility and economy of the desorption process into account, the method using a polar organic solvent and the like and the method using the change in pH are desirable, but a desorption method can be used without any particular limitation. In addition, when the adsorbent has an ability to change its color in response to an external stimulus such as heat, vibrations and light irradiation in the desorption process, the adsorption-desorption can be monitored simply.

An analysis system can be constructed by combining the solid phase extraction using the adsorbent of the invention. This analysis system has a solid phase extraction unit which includes the adsorbent of the invention and in which a solute in a sample is selectively adsorbed to the adsorbent and an analyzer to which the solute desorbed from the adsorbent is introduced and in which the solute is analyzed. In the analysis system, a sample containing impurities can be pretreated using the adsorbent of the invention. Through a highly efficient and highly selective pretreatment process, the eluate can be collected from the solid phase extraction unit and the solute adsorbed to and held by the adsorbent can be identified, for example using an analysis method such as mass spectrometry (MS), liquid chromatography (LC) and gas chromatography (GC) or a combination thereof. Moreover, even when a certain solute is contained in a tiny amount (<1 ng) in the sample, the eluted solution can be evaporated, and a solution obtained by dissolving the resulting substance can be introduced to the mobile phase of LC or LC/MS to analyze the solute. In the microanalysis, it is important to keep the loss of the solute during the pretreatment as low as possible. The loss of the solute during the pretreatment varies also with the sensitivity of the subject to be detected and its content, but the loss is preferably 20% or less of the total solute amount, more preferably 10% or less, further preferably 5% or less.

Figure 2:
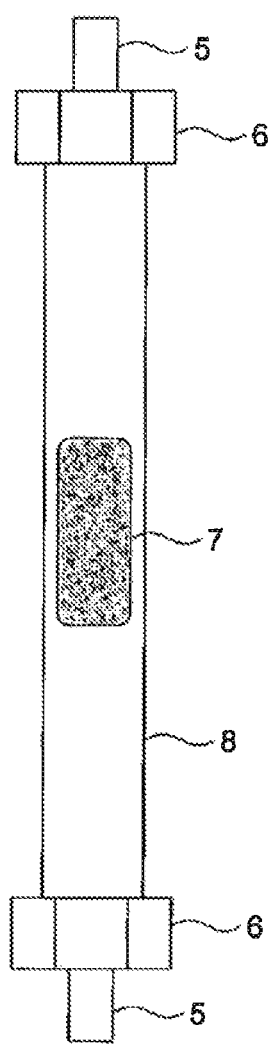
FIG. 2 A figure showing an embodiment of the solid phase extraction column of the invention.

Preferable forms of the solid phase extraction unit are a solid phase extraction cartridge and a solid phase extraction column. FIG. 1 shows an embodiment of the solid phase extraction cartridge, and FIG. 2 shows an embodiment of the solid phase extraction column. The solid phase extraction cartridge of FIG. 1 basically consists of a cartridge container upper part 1, a support filter 2 of the adsorbent, an adsorbent-filled part 3 and a cartridge container lower part 4. A change of the color of the adsorbent in the adsorbent-filled part 3 can be visually observed from outside.

The embodiment of the solid phase extraction column shown in FIG. 2 has a flow path 5 to which a sample is introduced and from which the sample is eluted, a column-integrally formed manually tightened nut, an adsorbent visual observation window 7 and an adsorbent-filled column 8. A change of the color of the adsorbent filled in the adsorbent-filled column 8 can be visually observed through the adsorbent visual observation window 7.

For example, when an elution solvent which changes the molecular structure of the adsorbent and which changes the color thereof, such as potassium hydroxide, is applied to a cartridge and a column filled with the adsorbent to which a solute is adsorbed, the color of the adsorbent changes from yellow (yellowish brown) to red, and the desorption of the solute can be visually observed. The shapes of the adsorbent-filled part 3 and the adsorbent visual observation window 7, the structures thereof and the materials thereof are not particularly limited as long as the visibility of the adsorbent is secured. For the purpose of further improving the visibility, a semitransparent or transparent material is desirably used. Moreover, in addition to visual observation, the change of the color can be detected by a method utilizing spectroscopy using transmitted light in the ultraviolet region, the visible region and the infrared region, reflected light, absorption or the like, and a method can be suitably selected in accordance with the constitution of the analysis system having the solid phase extraction unit. The solvents used in the washing process and the elution process may have a hydrogen ion concentration gradient if necessary or may be adopted to a special separation mode such as linear gradient elution and stepwise elution, and the desorption state of the solute can be confirmed by the color.

An advantage of the analysis system of the invention is that the eluted solution can be introduced directly to the analyzer for identifying the solute. This is a characteristic which could not be achieved with the conventional adsorbents and is achieved because an adsorbent which can adapt to a water-soluble solute has been obtained by introducing the specific aromatic side-chain functional group. In the prior art, it has been difficult to adsorb and hold a wide range of solutes and separate and recover the solutes by solid phase extraction, due to the ion suppression effect of the adsorbent in MS analysis and the polarity dependency of the solutes. That is, due to the ion suppression effect, unnecessary components are contained in the eluted solution, and the identification of the solute becomes extremely difficult. Moreover, the decrease in the amount of the recovered solute decreases the measurement sensitivity, and satisfactory analysis has been impossible. On the other hand, by performing pretreatment in the solid phase extraction unit including the adsorbent of the invention, cooperation with a liquid phase chromatography/ultraviolet spectrometer (LC-UV), a mass spectrometer using liquid phase chromatography (LC-MS), a mass spectrometer of a flow injection analysis type (FIA-MS), an HPLC device and other analyzers becomes easy. Moreover, when the adsorbent has an ability to change its color in the adsorption-desorption processes, the adsorption-desorption can be monitored simply by visually observing the change of the color in the solid phase extraction unit from the outside.

EXAMPLES

The invention is explained specifically below referring to Examples and Comparative Examples, but the invention is not limited to the examples.

(1) Measurement of Particle Size

The particle size of adsorbent particles was measured using a Microtrac particle size distribution analyzer manufactured by Nikkiso Co., Ltd. (Microtrac FRA, laser diffraction scattering system). The measurement range was 0.1 μm to 700 μm, and the 50% median particle size (the particle size at 50% on a cumulative curve, where the cumulative curve was derived with the total volume of the powder aggregation set at 100%) was regarded as the particle size of the adsorbent particles.

(2) Infrared Spectroscopic Measurement

The infrared (IR) spectroscopic measurement of adsorbent particles was performed using a Fourier transform infrared spectrometer manufactured by PerkinElmer Inc. (Spectrum 100, attenuated total reflection: ATR). With regard to all of the samples shown in the following Reference Examples, Examples and Comparative Examples, the molecular structures and the introduction of the functional groups were confirmed by the IR measurement.

(3) Measurement of Specific Surface Area and Pore Size

The specific surface area and the pore distribution were measured using a specific surface area analyzer manufactured by Quantachrome Instruments (AUTOSORB-1, multipoint (40-point measurement) measurement). The pretreatment of a measurement sample was performed under the condition of 120° C. and 10 minutes (reduced pressure). The specific surface area was calculated using a BET (Brunauer, Emmett, Teller) adsorption isotherm from the slope and the intercept of the BET plots. To determine the pore size, the pore distribution was calculated using the BJH (Barrett, Joyner, Halenda) method from the change in the cumulative pore volume, and the peak size of the distribution was regarded as the pore size.

(4) Measurement of Copolymerization Ratio by Elementary Analysis

The element ratio of carbon (C), hydrogen (H), nitrogen (N) and oxygen (O) was quantified by a combustion method, and the copolymerization ratio of adsorbent particles was determined from the composition ratio of the polymer particles. An elemental analyzer manufactured by Yanagimoto Seisakusho Co (MT-5) was used for the CHN-element analysis, and an elemental analyzer manufactured by J-Science Lab CO., Ltd. (model JM10) was used for the O-element analysis.

(5) Method for Filling Solid Phase Extraction Plate with Adsorbent Particles

An adsorbent was packed by the following method. Slurry of 4 mg of an adsorbent to be evaluated in methanol (100 μL to 200 μL) was prepared, and a solid phase extraction plate (manufactured by Waters Corporation, OASIS (registered trademark) μ-Elution plate) was filled with the slurry.

(6) Evaluation of Adsorption of Solute to Adsorbent (Solid Phase Extraction)

The target solutes used for the evaluation of the adsorption of solutes to adsorbents (solid phase extraction) were as follows. An evaluation aqueous medicine solution 1 (phenobarbital (log P=1.7, 25 ng/mL), phenytoin (log P=2.5, 25 ng/mL), carbamazepine (log P=2.5, 2.5 ng/mL) and diazepam (log P=2.9, 2.5 ng/mL), solvent: 20% aqueous methanol solution), an evaluation aqueous medicine solution 2 (theophylline (log P=−0.25, 5000 ng/mL), solvent: water), an evaluation aqueous medicine solution 3 (gemcitabine (log P=0.14, 1000 ng/mL), 5-fluorouracil (log P=−0.57, 1000 ng/mL) and tenofovir (log P=−1.5, 1000 ng/mL), solvent: water), an evaluation aqueous medicine solution 4 (methotrexate (MTX) (log P=−0.91, 1000 ng/mL), solvent: water) and an evaluation aqueous medicine solution 5: cytarabine (log P=−2.7, 1000 ng/mL), solvent: water) were prepared, and solid phase extraction of the respective aqueous solutions was performed.

The solid phase extraction was performed by the following method. Methanol in an amount of 200 μL and then purified water in an amount of 200 μL were applied to a solid phase extraction plate filled with an adsorbent. Then, 100 μL of a solution was added to the plate and sucked after being left still for one minute to apply the solution. Next, the adsorbent was washed by applying 200 μL of purified water to the plate. After washing, 100 μL of methanol was applied to the plate, and the solute adsorbed to the adsorbent was recovered. The recovery rate of the solid phase extraction was defined as the amount of the solute recovered by this operation relative to the charged amount. If necessary, a pH regulator or an additive may be added to the aqueous solutions.

The amount of a serum phospholipid (phosphatidylcholine (lecithin)) adsorbed to an adsorbent was evaluated by the following method. Methanol in an amount of 200 μL and then purified water in an amount of 200 μL were applied to a solid phase extraction plate filled with an adsorbent. Then, 100 μL of a solution was added to the plate, and 100 μL of commercial control serum was added. After leaving still for one minute, the solution was sucked, thereby applying the solution. Next, the adsorbent was washed by applying 200 μL of purified water to the plate. After washing, 100 μL of methanol was applied to the plate, and the peak height of the signal strength in LC-MS corresponding to the mass-to-charge ratio of phosphatidylcholine (m/z 758) was regarded as the amount of adsorbed phosphatidylcholine. Here, because the phosphatidylcholine content in serum cannot be determined accurately, it is difficult to evaluate the absolute quantity of adsorbed phosphatidylcholine. In the Examples, the adsorption of phosphatidylcholine was compared by the relative signal strengths, where the phospholipid was adsorbed under a certain condition and the signal strength of the highest peak was set as 100% to determine a relative strength. The measurement was performed three times, and the average value was regarded as the measurement results. In this regard, a solution to which an internal standard suitable for the target solute had been added when necessary was used for the LC-MS measurement.

An L-2000 series liquid chromatograph manufactured by Hitachi High-Technologies Corporation (model L-2100 pump (low pressure gradient, with a degasser), model L-2200 autosampler (with a cooling unit), model L-2400 UV detector (with a semi-micro flow cell) and model D-2000 HPLC system manager) was used for the LC-UV measurement. Capcell PAK C18 MG manufactured by Shiseido Co., Ltd. (particle size 3 μm, inside diameter 2.0 mm×length 75 mm) was used as the column of the LC unit.

An L-2000 series liquid chromatograph manufactured by Hitachi High-Technologies Corporation (model L-2100 pump (low pressure gradient, with a degasser), model L-2200 autosampler (with a cooling unit) and model D-2000 HPLC system manager) combined with a 3200 Qtrap mass spectrometer manufactured by Applied Biosystems was used for the LC-MS measurement. Capcell PAK C18 MG manufactured by Shiseido Co., Ltd. (particle size 3 μm, inside diameter 2.0 mm×length 75 mm) was used as the column of the LC unit. The ionization conditions were electrospray ionization and cation measurement, and the mode of mass spectroscopy scanning was mass scan (MS)+ product ion scan (MS/MS). The LC-MS measurement conditions were as follows. The eluents were a solution A (10 mM ammonium acetate/acetonitrile=90%/10%), a solution B (acetonitrile) and a solution C (isopropyl alcohol): the gradient conditions (solution A/solution B/solution C) were (70%/30%/0%) at 0 min, (0%/100%/0%) at 10 min, (0%/0%/100%) at 15 min, (0%/0%/100%) at 23 min, (70%/30%/0%) at 23.1 min and (70%/30%/0%) at 30 min: the flow rate was 0.2 mL/min: the sample injection amount was 5 μL: and the measurement period was 30 minutes.

An L-2000 series liquid chromatograph manufactured by Hitachi High-Technologies Corporation (model L-2100 pump (low pressure gradient, with a degasser), model L-2200 autosampler (with a cooling unit) and model D-2000 HPLC system manager) combined with a 3200 Qtrap mass spectrometer manufactured by Applied Biosystems was used for the FIA-MS measurement. The ionization conditions were electrospray ionization and cation measurement, and the mode of mass spectroscopy scanning was multiple reaction monitoring (MRM). The FIA-MS measurement conditions were as follows. The eluent was 10 mM ammonium acetate/acetonitrile=90%/10%: the flow rate was 0.1 mL/min: the sample injection amount was 10 μL: and the measurement period was 2.0 minutes.

Reference Example 1

Synthesis of Divinylbenzene-Vinylphenol Copolymer Particles

Divinylbenzene (DVB)-vinylphenol (VP) particles were synthesized through copolymerization of divinylbenzene and 4-vinylphenyl acetate (VPA) and hydrolysis of acetyl group. In a 500 mL separable flask, 2.0 g of hydroxypropyl cellulose (HPC, manufactured by Aldrich Corporation, average molecular weight ≤10,000, viscosity 5 cP (an aqueous 2 wt % solution, 20° C.)) and 100 mL of water were mixed and stirred until the HPC dissolved completely. Then, divinylbenzene (manufactured by Aldrich Corporation, a mixture of 80% divinylbenzene+19% ethylvinylbenzene) and 4-vinylphenyl acetate (manufactured by Tokyo Chemical Industry Co., Ltd.) in a total amount of 30 g were mixed, and 20 g of toluene (manufactured by Wako Pure Chemical Industries, Ltd.) and 0.4 g of azoisobutyronitrile (AIBN, manufactured by Tokyo Chemical Industry Co., Ltd.) were further added. After completely dissolving the substances, the solution was added to the separable flask. A nitrogen introduction tube and a cooling tube were connected to the separable flask, and the solution was stirred with a stirring blade for 30 minutes while substituting the atmosphere in the polymerization system with nitrogen. After the solution in the flask reached a uniformly dispersed state, polymerization was conducted at 70° C. for 20 hours at a stirring speed of 400 rpm. After stopping stirring, the polymerization solution and the resin particles were separated by filtration through a glass filter. The resin particles were repeatedly washed with purified water until the surfactant was completely removed, and then the resin particles were repeatedly washed with 2-butanone (manufactured by Wako Pure Chemical Industries, Ltd.), toluene (manufactured by Wako Pure Chemical Industries, Ltd.) and 2-butanone in this order. After drying at room temperature and then drying at 110° C. for 15 hours at reduced pressure, DVB-VPA resin particles were obtained (yield 95 to 99%).

Methanol (manufactured by Wako Pure Chemical Industries, Ltd.) in an amount of 20 mL and 20 mL of a 0.1 M aqueous solution of 1 M potassium hydroxide (manufactured by Wako Pure Chemical Industries, Ltd.) were added to 20 g of the precursor in a 300 mL round-bottomed flask, and the acetyl group was hydrolyzed by heating to reflux for 30 minutes. The resin particles were washed with 0.1 M hydrochloric acid (manufactured by Wako Pure Chemical Industries, Ltd.) and purified water and recovered. The charged ratios of DVB and VPA, the 50% mean particle sizes of DVB-VP and the copolymerization ratios (ratios by mole) of DVB and VP determined by elementary analysis after the hydrolysis are shown in Table 1. In addition, the molecular structures were identified by infrared spectroscopy, and the particles were observed with a microscope. As a result, it was confirmed that all the kinds of particles were spherical particles.

TABLE 1

| DVB:VPA Charged Ratio by Mole | DVB-VP 50% Mean Particle Size (μm) | Copolymerization Ratio | |
|---|---|---|---|
| | | DVB | VP |
| DVB:VPA = 9:1 | 33.2 | 88.7 mol % | 12.3 mol % |
| DVB:VPA = 7:3 | 32.1 | 70.7 mol % | 29.3 mol % |
| DVB:VPA = 5:5 | 29.3 | 48.9 mol % | 51.1 mol % |

Examples 1 to 3

Preparation of Nitrated Divinylbenzene-Vinylphenol Copolymer Particles

The DVB-VP copolymer particles prepared in Reference Example 1 were nitrated by the following method. Concentrated sulfuric acid (95+%, manufactured by Wako Pure Chemical Industries, Ltd.) in an amount of 5 g and concentrated nitric acid (about 1.38 g/ml, manufactured by Wako Pure Chemical Industries, Ltd.) in an amount of 20 g were mixed by stirring well to prepare a mixed acid. Then, 10 g of the DVB-VP particles, 10 mL of methanol (manufactured by Wako Pure Chemical Industries, Ltd.) and 10 mL of water were mixed in a 300 mL round-bottomed flask to disperse the particles, and then 25 g of the mixed acid was dropped gradually with a dropper in a water bath. After dropping the total amount, the solution was mixed for 10 minutes, and then the flask was heated to 50° C., followed by nitration for one hour. After the completion of the reaction, the resin particles were recovered by filtration and then stirred in purified water again for 30 minutes to wash the resin particles. An aqueous 0.1 M solution of potassium hydroxide (manufactured by Wako Pure Chemical Industries, Ltd.) was dropped to a dispersion of the resin particles to neutralize the dispersion, and then the resin particles were washed with 0.1 M hydrochloric acid (manufactured by Wako Pure Chemical Industries, Ltd.) and purified water and recovered. After washing, the resin particles were dried at 90° C. for 15 hours, and the target nitrated DVB-VP resin particles were obtained. Table 2 compares the physical properties of the DVB-VP copolymers which were prepared in Reference Example 1 and then nitrated in the Examples. In addition, the molecular structures were identified by infrared spectroscopy, and the particles were observed with a microscope. As a result, it was confirmed that all the kinds of particles were spherical particles. Based on the DVB-VP copolymerization ratios (ratios by mole) shown in Table 1, the ratios by mole of nitro group and VP (nitro group/VP) determined from the results of elementary analysis were 1.7 to 2.5. Here, because phenolic hydroxyl group is an electron donating functional group, it is presumed that nitro group was preferentially introduced to the phenol side chain. That is, it is presumed that in the structures, mononitrophenol, dinitrophenol, trinitrophenol and tetranitrophenol were contained as the phenolic side-chain functional groups.

the resin particles were repeatedly washed with 2-butanone (manufactured by Wako Pure Chemical Industries, Ltd.), toluene (manufactured by Wako Pure Chemical Industries, Ltd.) and 2-butanone in this order. After drying at room temperature and then drying at 110° C. for 15 hours at reduced pressure, resin particles were obtained. The yields were 95 to 99%. The charged ratios of DVB and VT and the 50% mean particle sizes are shown in Table 3. In addition, the molecular structures were identified by infrared spectroscopy, and the particles were observed with a microscope. As a result, it was confirmed that all the kinds of particles were spherical particles.

TABLE 3

| DVB:VT Charged Ratio by Mole | DVB-VT 50% Mean Particle Size (μm) |
|---|---|
| DVB:VT = 9:1 | 35.8 |
| DVB:VT = 7:3 | 36.2 |
| DVB:VT = 5:5 | 36.6 |

TABLE 2

| | DVB:VPA Charged Ratio by Mole | Copolymerization Ratio (From Table 1) DVB | Copolymerization Ratio (From Table 1) VP | 50% Mean Particle Size (μm) | Ratio by Mole of Nitro Group and VP (Nitro Group/VP) | Specific Surface Area (m²/g) | Pore Size (nm) |
|---|---|---|---|---|---|---|---|
| Example 1 | DVB:VPA = 9:1 | 88.7 mol % | 12.3 mol % | 33.5 | 2.5 | 590 | 3.9 |
| Example 2 | DVB:VPA = 7:3 | 70.7 mol % | 29.3 mol % | 33.1 | 1.9 | 400 | 3.7 |
| Example 3 | DVB:VPA = 5:5 | 48.9 mol % | 51.1 mol % | 30.3 | 1.7 | 270 | 3.8 |

Reference Example 2

Synthesis of Divinylbenzene-Vinyltoluene Copolymer Particles

As Reference Example 2, copolymer resins of divinylbenzene (DVB) and vinyltoluene (VT) were prepared by the following method. In a 500 mL separable flask, 2.0 g of hydroxypropyl cellulose (HPC, manufactured by Aldrich Corporation, average molecular weight ≤10,000, viscosity 5 cP (an aqueous 2 wt % solution, 20° C.)) and 100 mL of water were mixed and stirred until the HPC dissolved completely. Then, divinylbenzene (manufactured by Aldrich Corporation, a mixture of 80% divinylbenzene+19% ethylvinylbenzene) and vinyltoluene monomer (an m,p mixture, manufactured by Tokyo Chemical Industry Co., Ltd.) in a total amount of 30 g were mixed, and 20 g of toluene (manufactured by Wako Pure Chemical Industries, Ltd.) and 0.4 g of azoisobutyronitrile (AIBN, manufactured by Tokyo Chemical Industry Co., Ltd.) were further added. After completely dissolving the substances, the solution was added to the separable flask. A nitrogen introduction tube and a cooling tube were connected to the separable flask, and the solution was stirred with a stirring blade for 30 minutes while substituting the atmosphere in the polymerization system with nitrogen. After the solution in the flask reached a uniformly dispersed state, polymerization was conducted at 70° C. for 20 hours at a stirring speed of 300 rpm. After stopping stirring, the polymerization solution and the resin particles were separated by filtration through a glass filter. The resin particles were repeatedly washed with purified water until the surfactant was completely removed, and then Reference Example 3

Synthesis of Divinylbenzene-Vinylmethylaniline Copolymer Particles

Aniline was introduced to DVB-VT copolymers by the following method as Reference Example 3. Concentrated sulfuric acid (95+%, manufactured by Wako Pure Chemical Industries, Ltd.) in an amount of 5 g and concentrated nitric acid (about 1.38 g/ml, manufactured by Wako Pure Chemical Industries, Ltd.) in an amount of 25 g were mixed by stirring well to prepare a mixed acid. Then, 20 g of the DVB-VT particles of Reference Example 2, 20 mL of methanol (manufactured by Wako Pure Chemical Industries, Ltd.) and 10 mL of water were added to a 300 mL round-bottomed flask to disperse the particles, and then 30 g of the mixed acid was dropped gradually with a dropper in a water bath. After dropping the total amount, the solution was mixed for 10 minutes, and then the flask was heated to 50° C., followed by nitration for 30 minutes. After the completion of the reaction, the resin particles were recovered by filtration and then stirred in purified water again for 30 minutes to wash the resin particles. An aqueous 0.1 M solution of potassium hydroxide (manufactured by Wako Pure Chemical Industries, Ltd.) was dropped to a dispersion of the resin particles to neutralize the dispersion, and then the resin particles were washed with 0.1 M hydrochloric acid (manufactured by Wako Pure Chemical Industries, Ltd.) and purified water and recovered. After washing, the resin particles were dried at 110° C. for 15 hours, and a nitrated DVB-VT precursor was prepared.

To 20 g of the precursor, 20 g of tin granules (manufactured by Wako Pure Chemical Industries, Ltd.) and 20 mL of methanol (manufactured by Wako Pure Chemical Industries, Ltd.) were added and mixed, and 30 g of hydrochloric acid (about 35%, manufactured by Wako Pure Chemical Industries, Ltd.) was further added. By heating to reflux, the nitro group was reduced, and thus the precursor was converted to vinylmethylaniline (VMA). The resin particles were recovered by filtration, and a dispersion of the resin particles was washed with an aqueous 1 M solution of potassium hydroxide (manufactured by Wako Pure Chemical Industries, Ltd.) and purified water. The resin particles were recovered. After washing, the resin particles were dried at 110° C. for 15 hours, and the target DVB-VMA resin particles were obtained. Table 4 shows the 50% mean particle sizes and the copolymerization ratios (ratios by mole) of DVB and VMA. In addition, the molecular structures of the respective samples were identified by infrared spectroscopy, and the particles were observed with a microscope. As a result, it was confirmed that the particles of all of the samples were spherical particles.

TABLE 4

| DVB:VT Charged Ratio by Mole | DVB-VMA 50% Mean Particle Size (μm) | Copolymerization Ratio | |
|---|---|---|---|
| | | DVB | VMA |
| DVB:VT = 9:1 | 36.2 | 90.1 mol % | 9.9 mol % |
| DVB:VT = 7:3 | 36.3 | 69.2 mol % | 30.8 mol % |
| DVB:VT = 5:5 | 36.2 | 50.7 mol % | 49.3 mol % |

Examples 4 to 6

Preparation of Nitrated Divinylbenzene-Vinylmethylaniline Copolymer Particles

The DVB-VMA copolymer particles prepared in Reference Example 3 were nitrated by the following method.

First, acetic anhydride (manufactured by Wako Pure Chemical Industries, Ltd.) and the aniline in the DVB-VMA copolymer particles of Reference Example 3 were reacted to protect the aniline with acetyl. Then, 5 g of concentrated sulfuric acid (95+%, manufactured by Wako Pure Chemical Industries, Ltd.) and 20 g of concentrated nitric acid (about 1.38 g/ml, manufactured by Wako Pure Chemical Industries, Ltd.) were mixed by stirring well to prepare a mixed acid. Then, 10 g of the DVB-VMA particles, 10 mL of methanol (manufactured by Wako Pure Chemical Industries, Ltd.) and 10 mL of water were added to a 300 mL round-bottomed flask to disperse the particles, and then 25 g of the mixed acid was dropped gradually with a dropper in a water bath. After dropping the total amount, the solution was mixed for 10 minutes, and then nitration was conducted at room temperature for one hour. After the completion of the reaction, the resin particles were recovered by filtration and then stirred in purified water again for 30 minutes to wash the resin particles. Next, 1 M hydrochloric acid (manufactured by Wako Pure Chemical Industries, Ltd.) was added to a dispersion of the resin particles, and the acetyl protecting group was removed by heating to reflux for 30 minutes. After the completion of the reaction, the resin particles were recovered by filtration and then stirred in purified water again for 30 minutes to wash the resin particles. After an aqueous 1 M solution of potassium hydroxide (manufactured by Wako Pure Chemical Industries, Ltd.) was dropped thereto to neutralize the solution, the resin particles were washed with purified water and recovered. After washing, the resin particles were dried at 90° C. for 15 hours, and the target nitrated DVB-VMA resin particles were obtained. In addition, the molecular structures of the respective samples were identified by infrared spectroscopy, and the particles were observed with a microscope. As a result, it was confirmed that the particles of all of the samples were spherical particles.

The physical properties of the nitrated products of the DVB-VMA copolymers prepared in Reference Example 3 are shown in Table 5. Based on the DVB-VMA copolymerization ratios (ratios by mole) shown in Table 4, the ratios by mole of nitro group and VMA (nitro groupNMA) determined from the results of elementary analysis were 1.2 to 1.7. Here, because methyl group and amino group are electron donating functional groups, it is presumed that nitro group was preferentially introduced to the methylaniline side chain. That is, it is presumed that in the structures, mononitromethylaniline, dinitromethylaniline and trinitromethylaniline were contained as the methylaniline side-chain functional groups.

TABLE 5

| | DVB:VT Charged Ratio by Mole | Copolymerization Ratio (From Table 4) | | 50% Mean Particle Size (μm) | Ratio by Mole of Nitro Group and VMA (Nitro Group/VMA) | Specific Surface Area (m²/g) | Pore Size (nm) |
|---|---|---|---|---|---|---|---|
| | | DVB | VMA | | | | |
| Example 4 | DVB:VT = 9:1 | 90.1 mol % | 9.9 mol % | 35.9 | 1.7 | 610 | 4.2 |
| Example 5 | DVB:VT = 7:3 | 69.2 mol % | 30.8 mol % | 35.7 | 1.5 | 550 | 4.2 |
| Example 6 | DVB:VT = 5:5 | 50.7 mol % | 49.3 mol % | 35.8 | 1.2 | 490 | 4.1 |

Example 7

Preparation of Side-Chain-Nitrated Product of Silica Particles Having Phenol Side Chain Silica particles having a phenol side chain and the nitration method thereof are shown below. A silica gel carrier for a column chromatograph (manufactured by Wako Pure Chemical Industries, Ltd., Wakogel (registered trademark) C-400HG) was immersed in a methanol (manufactured by Wako Pure Chemical Industries, Ltd.) solution to which a silane coupling agent (manufactured by Shin-Etsu Chemical Co., Ltd., KBM-503) had been added at a concentration of 3% and dried at 80° C. so as to subject the silica gel carrier to coupling treatment. The carrier in an amount of 10 g was immersed in borane-tetrahydrofuran (THF) complex (a 1.0 M-THF solution, manufactured by Aldrich Corporation) in a nitrogen atmosphere and then stirred for 10 minutes. After filtering in air, the carrier was dispersed in a THF (manufactured by Wako Pure Chemical Industries, Ltd.) solution to which vinylphenol acetate (VPA) had been added at a concentration of 20% and heated and stirred in a nitrogen atmosphere at 60° C. for one hour, thereby immobilizing VPA on the surfaces of the silica particles. Here, borane-THF complex is known as a polymerization initiator which causes living radical polymerization, and the methacryl group on the surface subjected to the coupling treatment acts as the end at which the polymerization of VPA initiates through hydroboration by this method. The silica particles on which VPA was immobilized were repeatedly washed with purified water until the surfactant was completely removed, and then the silica particles were repeatedly washed with 2-butanone (manufactured by Wako Pure Chemical Industries, Ltd.), toluene (manufactured by Wako Pure Chemical Industries, Ltd.) and 2-butanone in this order. After drying at room temperature and then drying at 110° C. for 15 hours at reduced pressure, resin particles were obtained. The yield was 11.2 g, and the weight increased by about 10% after the VPA immobilization. In addition, the molecular structure of the sample was identified by infrared spectroscopy, and the particles were observed with a microscope. As a result, it was confirmed that the particles were spherical particles.

Hydrolysis of vinylphenol (VP) and nitration were performed by methods similar to those in Reference Example 1 and Examples 1 to 3, and silica particles having a phenol side chain and a phenol-side-chain-nitrated product were prepared. The weight of the silica particles was 11.0 g after the hydrolysis, and the weight after the nitration was 11.6 g. The ratio by mole of nitro group and VP (nitro groupNP) was calculated to be 1.4 from the increase in the VPA amount and the results of elementary analysis. It is presumed that a nitrophenol side chain was formed through the nitration of VP as in Examples 1 to 3.

Example 8

Preparation of Nitrated Divinylbenzene-Vinylphenol Copolymer Monolithic Column

The method for preparing a monolithic column containing divinylbenzene (DVB)-vinylphenol (VP) and the nitration method thereof are shown below. Divinylbenzene (manufactured by Aldrich Corporation, a mixture of 80% divinylbenzene+19% ethylvinylbenzene) in an amount of 13.0 g and 4-vinylphenyl acetate (manufactured by Tokyo Chemical Industry Co., Ltd.) in an amount of 7.0 g were mixed, and 10 g of toluene (manufactured by Wako Pure Chemical Industries, Ltd.) and 0.4 g of azoisobutyronitrile (AIBN, manufactured by Tokyo Chemical Industry Co., Ltd.) were further added. After completely dissolving the substances, the atmosphere of the solution was replaced with nitrogen. The monomer solution was poured into a cylindrical mold having the same shape as the filling part of the solid phase extraction plate, and bulk polymerization was performed in the mold at 80° C. for six hours in a nitrogen atmosphere.

Using the cured cylindrical compact, hydrolysis of vinylphenol (VP) and nitration were performed by methods similar to those in Reference Example 1 and Examples 1 to 3, and a nitrated divinylbenzene-vinylphenol copolymer monolithic column was prepared. The DVB-VP copolymerization ratio was DVB=72.1 mol %/VPA=27.9 mol %, and the ratio by mole of nitro group and VP (nitro group/VP) was calculated to be 1.7. It is presumed that a nitrophenol side chain was formed through the nitration of VP as in Examples 1 to 3 and 7. In addition, the molecular structure of the sample was identified by infrared spectroscopy, and the particles were observed with a microscope, thereby confirming that the intended structure was formed.

Comparative Example 1

Divinylbenzene Polymer

As Comparative Example 1, a resin of a divinylbenzene (DVB) homopolymer was prepared. In a 500 mL separable flask, 2.0 g of hydroxypropyl cellulose (HPC, manufactured by Aldrich Corporation, average molecular weight ≤10,000, viscosity 5 cP (an aqueous 2 wt % solution, 20° C.)) and 100 mL of water were mixed and stirred until the HPC dissolved completely. Then, 35.0 g (0.28 mol) of divinylbenzene (DVB, manufactured by Aldrich Corporation, a mixture of 80% divinylbenzene+19% ethylvinylbenzene), 24.2 g of toluene (manufactured by Wako Pure Chemical Industries, Ltd.) and 0.4 g of azoisobutyronitrile (AIBN, manufactured by Tokyo Chemical Industry Co., Ltd.) were mixed. After completely dissolving the substances, the solution was added to the separable flask. A nitrogen introduction tube and a cooling tube were connected to the separable flask, and the solution was stirred with a stirring blade for 30 minutes while substituting the atmosphere in the polymerization system with nitrogen. After the solution in the flask reached a uniformly dispersed state, polymerization was conducted at 70° C. for 20 hours at a stirring speed of 300 rpm. After stopping stirring, the polymerization solution and the resin particles were separated by filtration through a glass filter. The resin particles were repeatedly washed with purified water until the surfactant was completely removed, and then the resin particles were repeatedly washed with 2-butanone (manufactured by Wako Pure Chemical Industries, Ltd.), toluene (manufactured by Wako Pure Chemical Industries, Ltd.) and 2-butanone in this order. After drying at room temperature and then drying at 110° C. for 15 hours at reduced pressure, resin particles were obtained (yield 95.3%, 50% mean particle size 50.3 μm, specific surface area 895 $m^2$/g, and mean pore size 233 Å).

Comparative Example 2

Divinylbenzene-N-Vinylpyrrolidone Copolymer

As Comparative Example 2, a copolymer resin of divinylbenzene (DVB) and N-vinylpyrrolidone (NVP) was prepared. In a 500 mL separable flask, 2.0 g of hydroxypropyl cellulose (HPC, manufactured by Aldrich Corporation, average molecular weight ≤10,000, viscosity 5 cP (an aqueous 2 wt % solution, 20° C.)) and 100 mL of water were mixed and stirred until the HPC dissolved completely. Then, 17.5 g (0.14 mol) of divinylbenzene (DVB, manufactured by Aldrich Corporation, a mixture of 80% divinylbenzene+ 19% ethylvinylbenzene), 10.2 g (0.09 mol) of N-vinylpyrrolidone (NVP, manufactured by Tokyo Chemical Industry Co., Ltd.), 24.2 g of toluene (manufactured by Wako Pure Chemical Industries, Ltd.) and 0.2 g of azoisobutyronitrile (AIBN, manufactured by Tokyo Chemical Industry Co., Ltd.) were mixed. After completely dissolving the substances, the solution was added to the separable flask. A nitrogen introduction tube and a cooling tube were connected to the separable flask, and the solution was stirred with a stirring blade for 30 minutes while substituting the atmosphere in the polymerization system with nitrogen. After the solution in the flask reached a uniformly dispersed state, polymerization was conducted at 70° C. for 20 hours at a stirring speed of 300 rpm. After stopping stirring, the polymerization solution and the resin particles were separated by filtration through a glass filter. The resin particles were repeatedly washed with purified water until the surfactant was completely removed, and then the resin particles were repeatedly washed with 2-butanone (manufactured by Wako Pure Chemical Industries, Ltd.), toluene (manufactured by Wako Pure Chemical Industries, Ltd.) and 2-butanone in this order. After drying at room temperature and then drying at 110° C. for 15 hours at reduced pressure, resin particles were obtained (yield 81.2%, 50% mean particle size 66.5 µm, 80% mean particle size 78.9 µm, copolymerization ratio DVB/NVP=81.7 mol %/18.7 mol % (elementary analysis), specific surface area 527 m$^2$/g, and mean pore size 153 Å).

Comparative Example 3

Nitration of Divinylbenzene Polymer

As Comparative Example 3, resin particles were prepared by nitrating a DVB homopolymer resin. First, 30 g of concentrated sulfuric acid (95+%, manufactured by Wako Pure Chemical Industries, Ltd.) and 20 g of concentrated nitric acid (about 1.38 g/ml, manufactured by Wako Pure Chemical Industries, Ltd.) were mixed by stirring well to prepare a mixed acid. Then, 10 g of DVB particles and 15 mL of methanol (manufactured by Wako Pure Chemical Industries, Ltd.) were added to a 300 mL round-bottomed flask to disperse the particles, and then 50 g of the mixed acid was dropped gradually with a dropper in a water bath. After dropping the total amount, the solution was mixed for 10 minutes, and then the flask was heated to 65° C., followed by nitration for two hours. After the completion of the reaction, the resin particles were recovered by filtration and then stirred in purified water again for 30 minutes to wash the resin particles. An aqueous 0.1 M solution of potassium hydroxide (manufactured by Wako Pure Chemical Industries, Ltd.) was dropped to a dispersion of the resin particles to neutralize the dispersion, and then the resin particles were washed with 0.1 M hydrochloric acid (manufactured by Wako Pure Chemical Industries, Ltd.) and purified water and recovered. After washing, the resin particles were dried at 90° C. for 15 hours, and the target nitrated DVB resin particles were obtained (yield 13.1 g, 50% mean particle size 51.4 µm, specific surface area 752 m$^2$/g, mean pore size 242 Å, and ratio by mole of nitro group and DVB (nitro group/DVB) determined by elementary analysis=0.88).

Test Example 1

Figure 3:
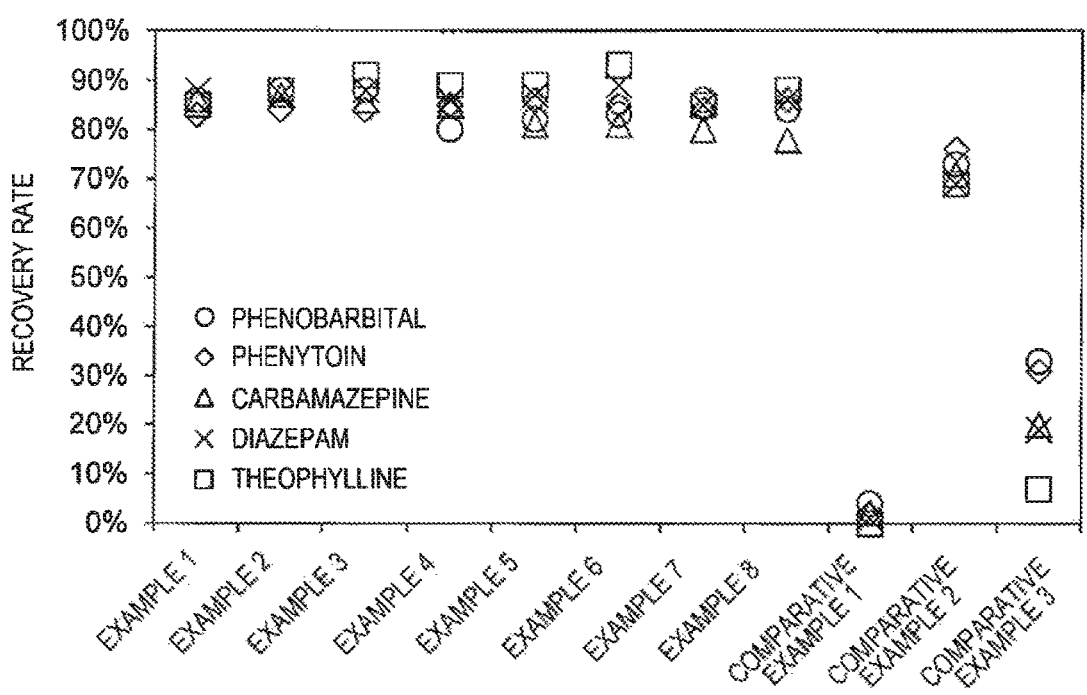
FIG. 3 A graph showing the recovery rates of solutes through solid phase extraction using the adsorbents of Examples 1 to 8 and Comparative Examples 1 to 3.
Figure 4:
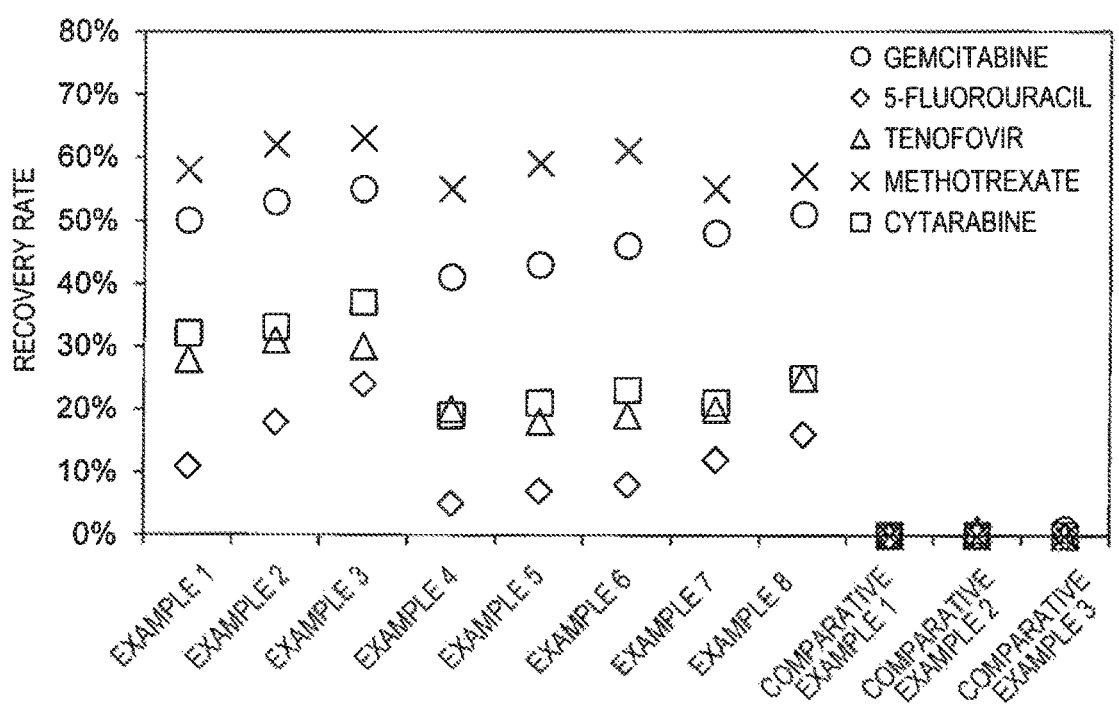
FIG. 4 A graph showing the recovery rates of solutes through solid phase extraction using the adsorbents of Examples 1 to 8 and Comparative Examples 1 to 3.

Comparison of Solid Phase Extraction Performance of Prepared Particles and Monolithic Column Using Solutes with Various Polarities Using the respective solutes (the evaluation aqueous medicine solutions 1 to 5), the solid phase extraction performance of the particles and the monolithic column shown in Examples 1 to 8 was compared by FIA-MS, and the results are summarized in FIGS. 3 and 4 and Table 6. The results showed that the adsorbents of Examples 1 to 8 had solid phase extraction performance with respect to all of the medicines. It is presumed that an unusual polarized structure was formed due to the electron donating and electron withdrawing groups of the nitrated side-chain functional group, and as a result, the property of recovering a medicine was acquired. In particular, the resin particles having nitrophenol on the side chain (Examples 1 to 3) showed recovery performance of about 10 to 20% also with respect to the medicines which are considered to be difficult to adsorb in general, such as 5-fluorouracil. The solid phase extraction was conducted only by the processes of application of the aqueous medicine solutions, washing and desorption, and no special solid phase extraction protocol was used. Accordingly, it is considered that the medicines were separated and recovered due to the medicine-adsorbing property peculiar to the adsorbents of the respective Examples. Furthermore, it was found that the adsorbents can be applied to any medicine kinds regardless of the log P value when the medicines have similar hydrophilicity and water-solubility.

In addition, the adsorbed medicines were easily desorbed by applying an organic solvent with high polarity such as methanol. In the Examples, no acidic or alkaline component was added to the eluents, and it is suggested that the medicines were adsorbed and held by a mechanism which is different from the adsorption mechanism of ion exchange using the conventional ion exchange resins. Furthermore, the adsorption performance tended to change with the log P of the medicine and the molecular structure; for example, the more side-chain functional groups the adsorbent had, the higher the recovery rate of 5-fluorouracil was.

On the other hand, the particles shown in Comparative Example 1 did not have a property of recovering any of the medicines at all. Moreover, although the particles shown in Comparative Examples 2 and 3 had a property of recovering the medicines of the groups of the evaluation aqueous medicine solutions 1 and 2, which had relatively high log P values, the particles did not have a property of recovering the medicines of the groups of the evaluation aqueous medicine solutions 3 to 5. It is presumed that this was because the polarity and the hydrophilicity of the side-chain functional groups contained in the adsorbents did not reach the levels at which the medicine groups could be adsorbed and held.

From the above results, it was demonstrated that an adsorbent having a specific molecular structure enables the recovery of water-soluble solutes, which are generally difficult to recover, and that a structure having nitrophenol has excellent performance in particular.

The structure and the introduction ratio of side chain of the adsorbent of the invention can be controlled in accordance with the kind of medicine. The side-chain functional group described in the invention is a structure also found in medicines, and it is considered to be a structure with high affinity to medicines. By controlling the molecular structure, a specific structure can be formed using intermolecular interaction such as association, hydrogen bond and self-assembly, and in addition to the polar structure of the adsorbent, acquisition of structural selectivity and application to molecular recognition function are also expected to be achieved.

TABLE 6

| | Solvent | Solute's Name | Example 1 | Example 2 | Example 3 | Example 4 | Example 5 | Example 6 |
|---|---|---|---|---|---|---|---|---|
| Evaluation Aqueous Medicine Solution 1 | 20% Aqueous Methanol Solution | Phenobarbital (25 ng/mL) | 86% | 88% | 88% | 80% | 82% | 83% |
| | | Phenytoin (2.5 ng/mL) | 83% | 84% | 84% | 85% | 86% | 85% |
| | | Carbamazepine (25 ng/mL) | 86% | 87% | 86% | 85% | 81% | 81% |
| | | Diazepam (2.5 ng/mL) | 88% | 87% | 88% | 86% | 87% | 89% |
| Evaluation Aqueous Medicine Solution 2 | Water | Theophylline (25 ng/mL) | 85% | 88% | 91% | 89% | 89% | 93% |
| Evaluation Aqueous Medicine Solution 3 | Water | Gemcitabine (1000 ng/mL) | 50% | 53% | 55% | 41% | 43% | 46% |
| | | 5-Fluorouracil (1000 ng/mL) | 11% | 18% | 24% | 5% | 7% | 8% |
| | | Tenofovir (1000 ng/mL) | 28% | 31% | 30% | 20% | 18% | 19% |
| Evaluation Aqueous Medicine Solution 4 | Water | Methotrexate (1000 ng/mL) | 58% | 62% | 63% | 55% | 59% | 61% |
| Evaluation Aqueous Medicine Solution 5 | Water | Cytarabine (1000 ng/mL) | 32% | 33% | 37% | 19% | 21% | 23% |

| | Solvent | Solute's Name | Example 7 | Example 8 | Comparative Example 1 | Comparative Example 2 | Comparative Example 3 |
|---|---|---|---|---|---|---|---|
| Evaluation Aqueous Medicine Solution 1 | 20% Aqueous Methanol Solution | Phenobarbital (25 ng/mL) | 86% | 84% | 4% | 73% | 33% |
| | | Phenytoin (2.5 ng/mL) | 84% | 86% | 2% | 76% | 31% |
| | | Carbamazepine (25 ng/mL) | 80% | 78% | 2% | 71% | 20% |
| | | Diazepam (2.5 ng/mL) | 85% | 86% | 1% | 69% | 19% |
| Evaluation Aqueous Medicine Solution 2 | Water | Theophylline (25 ng/mL) | 85% | 88% | 0% | 69% | 7% |
| Evaluation Aqueous Medicine Solution 3 | Water | Gemcitabine (1000 ng/mL) | 48% | 51% | 0% | 0% | 1% |
| | | 5-Fluorouracil (1000 ng/mL) | 12% | 16% | 0% | 0% | 0% |
| | | Tenofovir (1000 ng/mL) | 20% | 25% | 0% | 1% | 0% |
| Evaluation Aqueous Medicine Solution 4 | Water | Methotrexate (1000 ng/mL) | 55% | 57% | 0% | 0% | 0% |
| Evaluation Aqueous Medicine Solution 5 | Water | Cytarabine (1000 ng/mL) | 21% | 25% | 0% | 0% | 0% |

Test Example 2

Comparison of Solid Phase Extraction Performance of Nitrated Particles with Detectors Using the evaluation aqueous medicine solution 1, the solid phase extraction performance of the particles prepared in Examples 1 to 3 was measured by LC-UV, LC-MS and FIA-MS, and the results of the comparison thereof are shown in Table 7. It was shown that the particles of Examples 1 to 3 all had a property of recovering the medicine by solid phase extraction at almost the same level and that accurate quantification was possible by all of the measurement methods. In addition, because the property of recovering a medicine was at almost the same level also when other evaluation aqueous medicine solutions were used, various constitutions can be used as the analysis system of the invention, and solid phase extraction and quantification of hydrophilic, water-soluble solutes are possible.

TABLE 7

| Solute's Name | Solvent | Measurement Apparatus | Example 1 | Example 2 | Example 3 |
|---|---|---|---|---|---|
| Phenobarbital (25 ng/mL) | 20% Aqueous Methanol Solution | LC-UV | 83% | 85% | 85% |
| | | LC-MS | 87% | 91% | 88% |
| | | FIA-MS | 86% | 88% | 88% |
| Phenytoin (2.5 ng/mL) | | LC-UV | 82% | 85% | 86% |
| | | LC-MS | 86% | 87% | 88% |
| | | FIA-MS | 83% | 84% | 84% |
| Carbamazepine | | LC-UV | 85% | 87% | 88% |

TABLE 7-continued

| Solute's Name | Solvent | Measurement Apparatus | Example 1 | Example 2 | Example 3 |
|---|---|---|---|---|---|
| (25 ng/mL) | | LC-MS | 87% | 88% | 88% |
| | | FIA-MS | 86% | 87% | 86% |
| Diazepam | | LC-UV | 89% | 90% | 91% |
| (2.5 ng/mL) | | LC-MS | 89% | 90% | 90% |
| | | FIA-MS | 88% | 87% | 88% |

Test Example 3

Evaluation of Amount of Adsorbed Phospholipid (Phosphatidylcholine)

When a solute such as serum and whole blood components is analyzed, impurity components such as phospholipids are contained. Impurities such as phospholipids are components which inhibit the ionization of the subject to be measured during mass spectrometry (ion suppression). In an apparatus including a chromatograph separation process such as LC-MS, the subject to be measured and the impurity components are separated, and thus the influence is small. However, in a flow injection analysis like FIA-MS, the influence of the decrease in the sensitivity due to the ion suppression is particularly significant. As shown below, according to the invention, the adsorption of the impurity components such as phospholipids can be reduced.

Using the adsorbents shown in Examples 1 to 3 and Comparative Examples 2 and 3, the relative strengths of the signal peaks of a phospholipid (the signal peaks corresponding to the mass-to-charge ratio (m/z 758) of phosphatidylcholine (PC), which is a kind of phospholipid) were evaluated. The results are shown in Table 8. Here, the relative strengths of PC are the strengths relative to the peak height (100%) of Comparative Example 2, in which the peak height of the signal strength of LC-MS was the highest. The results showed that the peak strengths of the adsorbents of Examples 1 to 3 tended to be weaker than those of the Comparative Examples with respect to serum samples which were treated under the same condition. It is considered that the adsorbents of Examples 1 to 3 maintained a very high level of surface hydrophilicity, and as a result, the adsorption of phospholipids such as phosphatidylcholine (PC) was inhibited. In this regard, further decrease is expected by studying the control of the surfaces of the particles of the Examples, such as the hydrophilicity and the pore structures.

The above results showed that an adsorbent suitable for isolating solutes with a wide range of chromatographic polarity can be obtained using the particles of the invention and that impurity components can be separated and removed. Moreover, when a column or a cartridge filled with the particles of the invention is used, an analysis system by solid phase extraction can be constructed.

TABLE 8

| | Example 1 | Example 2 | Example 3 | Comparative Example 2 | Comparative Example 3 |
|---|---|---|---|---|---|
| Signal Peak Relative Strength (m/z 758 LC-MS) | 48% | 45% | 44% | 100% | 81% |

Test Example 4

Change of Structures and Colors of Nitrated Adsorbents Through Alkali Immersion

The particles prepared in Examples 1 to 3 and 7 and the monolithic column of Example 8 were immersed in an aqueous dilute alkali solution, and the change of the molecular structures, the change of the colors and the change of the medicine recovery properties were studied. The results are shown below. The particles shown in Examples 1 to 3 and 7 and the monolithic column of Example 8 were immersed in an aqueous dilute potassium hydroxide solution which was adjusted to pH=8.0, washed and then dried at 90° C. for 15 hours, and aqueous alkali solution-immersed samples were prepared. Table 9 shows the color change of the samples after the alkali treatment, the 50% mean particle sizes and the ratios by mole of nitro group and the side-chain functional group determined by elementary analysis, and the measurement results of the specific surface areas and the pore sizes of Examples 1 to 3 only are shown. By immersing in the aqueous dilute alkali solution, the colors of all of the samples changed from yellow (yellowish brown) to red. On the other hand, the 50% mean particle sizes and the ratios by mole of nitro group and the side-chain functional group did not particularly change, and the appearances and the composition ratios of the elements did not change. From the results, it is considered that the structural change of the samples due to degradation or oxidation was not caused. On the contrary, decrease in the specific surface areas and change in the pore sizes were observed after the alkali treatment, and the tendency was more significant especially when the samples contained many nitro groups. In addition, because shifts in the infrared absorption spectra were also observed, it is presumed that protons were removed from the phenolic hydroxyl groups through the immersion in the aqueous dilute alkali solution, and the change of the polarized structures inside the samples, the induction of hydrogen bond or the like affected the colors, the specific surface areas and the pore sizes.

Moreover, the solid phase extraction performance measured by FIA-MS using the solutes (the evaluation aqueous medicine solutions 1 to 5) was compared, and the results are summarized in Table 10. With respect to all of the particles described in the Examples, the adsorption performance deteriorated significantly after the immersion in the aqueous dilute alkali solution.

The alkali-immersed particles and monolithic column which turned into red were immersed again in an aqueous 0.1 M hydrochloric acid solution, and the comparison of the physical properties and the measurement results of the medicine recovery rates are shown in Tables 9 and 10, respectively. By being subjected to acid treatment again, the samples turned into yellow (yellowish brown), which was the color before the alkali treatment, and the physical properties, namely the specific surface areas and the pore sizes, were at the same levels as those of the original particles. In addition, as shown in Table 10, it was confirmed that the recovery rates of the aqueous medicine solutions measured by FIA-MS also increased to the levels before the alkali treatment.

From the above results, it is considered that the polarized state inside the adsorbent and the molecular structure greatly affect the solid phase extraction performance. The change in the performance was not observed with the adsorbent particles shown in the Comparative Examples and is presumed to be a phenomenon peculiar to the adsorbent structure of the invention.

an aqueous dilute alkali solution is shown below. During the solid phase extraction, the solutes adsorbed to the adsorbents were recovered using 100 μL of an aqueous dilute potassium

TABLE 9

| | DVB:VPA Charged Ratio by Mole | | Color of Sample | 50% Mean Particle Size (μm) | Ratio by Mole of Nitro Group and VP (Nitro Group/VP) | Specific Surface Area (m$^2$/g) | Pore Size (nm) |
|---|---|---|---|---|---|---|---|
| Example 1 | DVB:VPA = 9:1 | Before Treatment | Yellow | 33.5 | 2.5 | 590 | 3.9 |
| | | After Alkali Treatment | Red | 33.5 | 2.5 | 290 | 4.1 |
| | | Alkali→Acid Treatment | Yellow | 33.5 | 2.5 | 610 | 3.9 |
| Example 2 | DVB:VPA = 7:3 | Before Treatment | Yellowish Brown | 33.1 | 1.9 | 400 | 3.9 |
| | | After Alkali Treatment | Red | 33.0 | 1.9 | 160 | 4.4 |
| | | Alkali→Acid Treatment | Yellowish Brown | 33.1 | 1.9 | 410 | 3.7 |
| Example 3 | DVB:VPA = 5:5 | Before Treatment | Yellowish Brown | 30.3 | 1.7 | 270 | 3.8 |
| | | After Alkali Treatment | Red | 30.4 | 1.7 | 20 | (Unable to measure) |
| | | Alkali→Acid Treatment | Yellowish Brown | 30.4 | 1.7 | 290 | 3.8 |
| Example 7 | (Silica-VP Surface Treatment + Nitration) | Before Treatment | Yellowish Brown | 29.8 | 1.4 | — | — |
| | | After Alkali Treatment | Red | 29.8 | 1.4 | — | — |
| | | Alkali→Acid Treatment | Yellowish Brown | 29.8 | 1.4 | — | — |
| Example 8 | (Nitrated DVB-VP Monolithic Column) | Before Treatment | Yellowish Brown | — | 1.7 | — | — |
| | | After Alkali Treatment | Red | — | 1.7 | — | — |
| | | Alkali→Acid Treatment | Yellowish Brown | — | 1.7 | — | — |

TABLE 10

| | Solvent | Solute's Name | | Example 1 | Example 2 | Example 3 | Example 7 | Example 8 |
|---|---|---|---|---|---|---|---|---|
| Evaluation Aqueous Medicine Solution 1 | 20% Aqueous Methanol Solution | Phenobarbital (25 ng/mL) | Before Treatment | 86% | 88% | 88% | 86% | 84% |
| | | | After Alkali Treatment | 19% | 22% | 20% | 18% | 26% |
| | | | Alkali→Acid Treatment | 83% | 87% | 85% | 86% | 86% |
| | | Phenytoin (2.5 ng/mL) | Before Treatment | 83% | 84% | 84% | 84% | 86% |
| | | | After Alkali Treatment | 33% | 31% | 27% | 22% | 24% |
| | | | Alkali→Acid Treatment | 84% | 85% | 85% | 82% | 84% |
| | | Carbamazepine (25 ng/mL) | Before Treatment | 86% | 87% | 86% | 80% | 78% |
| | | | After Alkali Treatment | 29% | 25% | 24% | 18% | 22% |
| | | | Alkali→Acid Treatment | 82% | 85% | 88% | 79% | 81% |
| | | Diazepam (2.5 ng/mL) | Before Treatment | 88% | 87% | 88% | 85% | 86% |
| | | | After Alkali Treatment | 39% | 33% | 37% | 28% | 31% |
| | | | Alkali→Acid Treatment | 85% | 88% | 90% | 81% | 79% |
| Evaluation Aqueous Medicine Solution 2 | Water | Theophylline (25 ng/mL) | Before Treatment | 85% | 88% | 91% | 85% | 88% |
| | | | After Alkali Treatment | 10% | 13% | 14% | 9% | 14% |
| | | | Alkali→Acid Treatment | 85% | 86% | 88% | 83% | 84% |
| Evaluation Aqueous Medicine Solution 3 | Water | Gemcitabine (1000 ng/mL) | Before Treatment | 50% | 53% | 55% | 48% | 51% |
| | | | After Alkali Treatment | 0% | 0% | 0% | 0% | 0% |
| | | | Alkali→Acid Treatment | 48% | 53% | 54% | 50% | 50% |
| | | 5-Fluorouracil (1000 ng/mL) | Before Treatment | 11% | 18% | 24% | 12% | 16% |
| | | | After Alkali Treatment | 0% | 0% | 0% | 0% | 0% |
| | | | Alkali→Acid Treatment | 10% | 17% | 25% | 14% | 18% |
| | | Tenofovir (1000 ng/mL) | Before Treatment | 28% | 31% | 30% | 20% | 25% |
| | | | After Alkali Treatment | 0% | 0% | 0% | 0% | 0% |
| | | | Alkali→Acid Treatment | 30% | 31% | 31% | 21% | 27% |
| Evaluation Aqueous Medicine Solution 4 | Water | Methotrexate (1000 ng/mL) | Before Treatment | 58% | 62% | 63% | 55% | 57% |
| | | | After Alkali Treatment | 0% | 0% | 0% | 0% | 0% |
| | | | Alkali→Acid Treatment | 61% | 64% | 62% | 55% | 58% |
| Evaluation Aqueous Medicine Solution 5 | Water | Cytarabine (1000 ng/mL) | Before Treatment | 32% | 33% | 37% | 21% | 25% |
| | | | After Alkali Treatment | 0% | 0% | 0% | 0% | 0% |
| | | | Alkali→Acid Treatment | 31% | 35% | 36% | 25% | 27% |

Test Example 5

Solid Phase Extraction of Medicines Using Color Change by Aqueous Dilute Alkali Solution The experiment of solid phase extraction of medicines with the particles shown in Examples 1 to 3 and 7 and the monolithic column of Example 8 using the color change by an aqueous dilute alkali solution is shown below. During the solid phase extraction, the solutes adsorbed to the adsorbents were recovered using 100 μL of an aqueous dilute potassium hydroxide solution with a hydrogen ion concentration adjusted to pH=8.0, instead of applying 100 μL of methanol to the plate, in the process of recovering the medicines adsorbed to the adsorbents, in the operations shown in "(6) Evaluation of Adsorption of Solute to Adsorbent (Solid Phase Extraction)" described above. The solid phase extraction performance with respect to the evaluation aqueous medicine solutions 1 to 5 was evaluated using FIA-MS, and the results are summarized in Table 11. Unlike the results of Test Example 4, it was shown that the medicines could be recovered from the aqueous medicine solutions under all of the conditions. The applied aqueous potassium hydroxide solution showed the effect at a low concentration and a tiny amount, and it is suggested that the molecular states of the surfaces and the adsorption performance were greatly influenced. Moreover, it is presumed that the change of the surface states had an effect similar to that when methanol was applied, and as a result, the medicines were eluted. Furthermore, as compared to the results of Test Example 1, 90% or more of the medicines could be generally recovered, and the medicines can be separated by performance comparable to that of the extraction using methanol.

In addition, the colors of the particles shown in Examples 1 to 3 changed from yellow (yellowish brown) to red when the aqueous dilute potassium hydroxide solution was applied, and it is suggested that the structures of the side-chain functional groups changed. As a result, it is possible to visually observe the elution of the adsorbed medicine with the change of the particle color. That is, by controlling the hydrogen ion concentration of the solvent, the adsorption-elution of the solute to/from the adsorbent can be freely controlled. Moreover, in the respective processes of adsorption, washing and elution, the solvent used can be water only, and the use of an organic solvent, which is volatile, inflammable and the like, is prevented. By constructing an analysis system having a solid phase extraction device using an adsorbent having the characteristics, solid phase extraction and quantification of hydrophilic, water-soluble solutes are possible.

REFERENCE SIGNS LIST

1: Cartridge container upper part
2: Support filter
3: Adsorbent-filled part
4: Cartridge container lower part
5: Flow path
6: Column-integrally formed manually tightened nut
7: Adsorbent visual observation window
8: Adsorbent-filled column All of the publications, patents and patent applications cited in the description are incorporated in the description by way of reference.

The invention claimed is:

1. An adsorbent comprising a structure represented by the formula I,

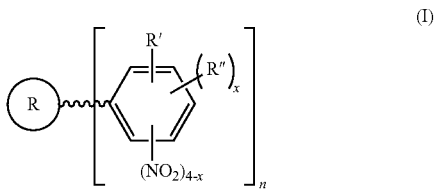

wherein R is a carrier component, wherein the carrier component is selected from the group consisting of inorganic compounds and polymers of organic compounds;

the moiety other than R is a side-chain functional group,

TABLE 11

|  | Solvent | Solute's Name | Example 1 | Example 2 | Example 3 | Example 7 | Example 8 |
|---|---|---|---|---|---|---|---|
| Evaluation Aqueous Medicine Solution 1 | 20% Aqueous Methanol Solution | Phenobarbital (25 ng/mL) | 80% | 83% | 81% | 78% | 77% |
|  |  | Phenytoin (2.5 ng/mL) | 79% | 77% | 78% | 81% | 80% |
|  |  | Carbamazepine (25 ng/mL) | 81% | 80% | 79% | 77% | 75% |
|  |  | Diazepam (2.5 ng/mL) | 80% | 79% | 80% | 78% | 79% |
| Evaluation Aqueous Medicine Solution 2 | Water | Theophylline (25 ng/mL) | 81% | 83% | 85% | 81% | 83% |
| Evaluation Aqueous Medicine Solution 3 | Water | Gemcitabine (1000 ng/mL) | 48% | 51% | 52% | 45% | 48% |
|  |  | 5-Fluorouracil (1000 ng/mL) | 9% | 16% | 20% | 9% | 13% |
|  |  | Tenofovir (1000 ng/mL) | 26% | 28% | 28% | 19% | 21% |
| Evaluation Aqueous Medicine Solution 4 | Water | Methotrexate (1000 ng/mL) | 55% | 59% | 60% | 49% | 50% |
| Evaluation Aqueous Medicine Solution 5 | Water | Cytarabine (1000 ng/mL) | 28% | 30% | 35% | 21% | 25% |

The invention is not limited to the embodiments and includes various modification examples. For example, part of the constitutions of the embodiments can be deleted or replaced with other constitutions, or other constitutions can be added.

R and the benzene ring in the side-chain functional group are bonded directly or bonded through one or more atoms, R' is selected from the group consisting of hydroxy group, alkoxy group, amino group, alkylamino group, thiol group and alkyl sulfide group, R" is independently selected from the group consisting of alkoxy group, alkyl group, amino group, alkylamino group, dialkylamino group, trialkylamino group, thiol group, alkyl sulfide group and hydrogen atom, x is an integer of zero or more and three or less, and n is the number of the side-chain functional groups contained in the carrier component, wherein the adsorbent adsorbs organic molecules, wherein the adsorbent is in the shape of spherical or aggregated particles, and wherein a 50% mean particle size of the adsorbent particles is in the range of 0.5 µm to 100 µm.

2. The adsorbent according to claim 1, wherein R in the formula I is a carrier component comprising a resin.

3. The adsorbent according to claim 1, wherein in the formula I, R' is hydroxy group, and R" is independently selected from the group consisting of alkoxy group, alkyl group and hydrogen atom.

4. The adsorbent according to claim 1, wherein in the formula I, R' is amino group, and R" is independently selected from the group consisting of alkoxy group, alkyl group and hydrogen atom.

5. The adsorbent according to claim 1, wherein the color changes in response to an external stimulus.

6. The adsorbent according to claim 1, wherein the color changes by contact with a basic solution having a hydrogen ion exponent higher than 8.0.

7. The adsorbent according to claim 2 which has a monolithic polymeric porous structure or a polymeric porous film structure.

8. An analysis system having a solid phase extraction unit which comprises the adsorbent according to claim 1 and in which a solute in a sample is selectively adsorbed to the adsorbent and an analyzer to which the solute desorbed from the adsorbent is introduced and in which the solute is analyzed, wherein the solute is an organic molecule.

9. The analysis system according to claim 8, wherein the analyzer is a liquid phase chromatography/ultraviolet spectrometer, a mass spectrometer using liquid phase chromatography or a mass spectrometer of a flow injection analysis type.

10. The analysis system according to claim 8, wherein the sample comprises plasma, serum, blood, urine, a spinal fluid, a synovial fluid, a tissue extract, an aqueous solution, groundwater, surface water, a soil extract, a cosmetic, a food material or an extract of a food material.

11. The analysis system according to claim 8, wherein the solute is a medicament, a medicine, an antibacterial agent, an antiviral agent, an anticancer agent, a drug, an insecticide, a herbicide, a poisonous substance, a biomolecule, a protein, a vitamin, a hormone, a polypeptide, a polynucleotide, a lipid, a carbohydrate, a contaminated substance, a metabolic agent or a decomposition product of a degraded metabolite.

12. The analysis system according to claim 8, wherein the solid phase extraction unit is a solid phase extraction cartridge or a solid phase extraction column.

13. The analysis system according to claim 8, wherein a change of the color of the adsorbent in the solid phase extraction unit can be visually observed from outside.

* * * * *